United States Patent
Venditti et al.

(10) Patent No.: US 10,307,469 B2
(45) Date of Patent: **\*Jun. 4, 2019**

(54) SYNTHETIC METHYLMALONYL-COA MUTASE TRANSGENE FOR THE TREATMENT OF MUT CLASS METHYLMALONIC ACIDEMIA (MMA)

(71) Applicant: The United States of America, as represented by the Secretary, Dept. of Health and Human Services, Washington, DC (US)

(72) Inventors: Charles P. Venditti, Potomac, MD (US); Randy J. Chandler, Washington, DC (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/633,964

(22) Filed: Jun. 27, 2017

(65) Prior Publication Data

US 2017/0326212 A1 Nov. 16, 2017

Related U.S. Application Data

(63) Continuation of application No. 14/773,885, filed as application No. PCT/US2014/028045 on Mar. 14, 2014, now Pat. No. 9,719,080.

(60) Provisional application No. 61/792,081, filed on Mar. 15, 2013.

(51) Int. Cl.
| | | |
|---|---|---|
| A61K 38/52 | (2006.01) | |
| C12N 9/90 | (2006.01) | |
| A61K 48/00 | (2006.01) | |

(52) U.S. Cl.
CPC .......... *A61K 38/52* (2013.01); *A61K 48/0066* (2013.01); *C12N 9/90* (2013.01); *C12Y 504/99002* (2013.01)

(58) Field of Classification Search
CPC .............................. C12N 9/90; A61K 48/0066
See application file for complete search history.

(56) References Cited

U.S. PATENT DOCUMENTS

| | | | |
|---|---|---|---|
| 7,358,351 B2 * | 4/2008 | St. Croix | C07K 16/30 435/91.1 |
| 7,745,391 B2 | 6/2010 | Mintz | |
| 8,999,380 B2 * | 4/2015 | Bancel | A61K 48/005 424/450 |
| 9,719,080 B2 * | 8/2017 | Venditti | C12N 9/90 |
| 9,944,918 B2 | 4/2018 | Venditti et al. | |

FOREIGN PATENT DOCUMENTS

WO  WO 2013/151666  10/2013

OTHER PUBLICATIONS

Carrillo-Carrasco et al. Hum Gene Ther 2010;21:1147-54.*
Bahr et al. (2004) GenBank Accession No. CR857121.1.
International Search Report and Written Opinion dated Sep. 16, 2014 for PCT/US2014/028045.
Ledley et al. (1988) Proc. Natl. Sci. USA 85:3518-3521 "Molecular cloning of L-methylmalonyl-CoA mutase: Gene transfer and analysis of mut cell lines".
Senac et al. (2012) Gene Therapy 19:385-391 "Gene therapy in a murine model of methylmalonic academia using rAAV9-mediated gene delivery".
Chandler et al. (2017) FASEB, J. 23(4):1252-1261, "Mitochondrial dysfunction in mut methylmalonic acidemia".
Chandler et al. (2010) Mole. Ther. 18:11-16, "Long-term Rescue of a Lethal Murine Model of Methylmalonic Acidemia Using Adeno-associated Viral Gene Therapy".
Handel et al. (2012) Human Gene Therapy 23:321-329 "Versatile and Efficient Genome Editing in Human Cells by Combining Zinc-Finger Nucleases With Adeno-Associated Viral Vectors".

\* cited by examiner

*Primary Examiner* — Scott Long
(74) *Attorney, Agent, or Firm* — Adsero IP

(57) ABSTRACT

Synthetic polynucleotides encoding human methylmalonyl-CoA mutase (synMUT) and exhibiting augmented expression in cell culture and/or in a subject are described herein. An adeno-associated viral (AAV) gene therapy vector encoding synMUT under the control of a liver-specific promoter (AAV2/8-HCR-hAAT-synMUT-RBG) successfully rescued the neonatal lethal phenotype displayed by methylmalonyl-CoA mutase-deficient mice, lowered circulating methylmalonic acid levels in the treated animals, and resulted in prolonged hepatic expression of the product of synMUT transgene in vivo, human methylmalonyl-CoA mutase (MUT).

11 Claims, 17 Drawing Sheets

Specification includes a Sequence Listing.

Figure 1

_Homo sapiens_ [gbpri]: 93487 CDS's (40662582 codons)

fields: [triplet] [frequency: per thousand] ([number])

```
UUU 17.6(714298)   UCU 15.2(618711)   UAU 12.2(495699)   UGU 10.6(430311)
UUC 20.3(824692)   UCC 17.7(718892)   UAC 15.3(622407)   UGC 12.6(513028)
UUA  7.7(311881)   UCA 12.2(496448)   UAA  1.0( 40285)   UGA  1.6( 63237)
UUG 12.9(525688)   UCG  4.4(179419)   UAG  0.8( 32109)   UGG 13.2(535595)

CUU 13.2(536515)   CCU 17.5(713233)   CAU 10.9(441711)   CGU  4.5(184609)
CUC 19.6(796638)   CCC 19.8(804620)   CAC 15.1(613713)   CGC 10.4(423516)
CUA  7.2(290751)   CCA 16.9(688038)   CAA 12.3(501911)   CGA  6.2(250760)
CUG 39.6(1611801)  CCG  6.9(281570)   CAG 34.2(1391973)  CGG 11.4(464485)

AUU 16.0(650473)   ACU 13.1(533609)   AAU 17.0(689701)   AGU 12.1(493429)
AUC 20.8(846466)   ACC 18.9(768147)   AAC 19.1(776603)   AGC 19.5(791383)
AUA  7.5(304565)   ACA 15.1(614523)   AAA 24.4(993621)   AGA 12.2(494682)
AUG 22.0(896005)   ACG  6.1(246105)   AAG 31.9(1295568)  AGG 12.0(486463)

GUU 11.0(448607)   GCU 18.4(750096)   GAU 21.8(885429)   GGU 10.8(437126)
GUC 14.5(588138)   GCC 27.7(1127679)  GAC 25.1(1020595)  GGC 22.2(903565)
GUA  7.1(287712)   GCA 15.8(643471)   GAA 29.0(1177632)  GGA 16.5(669873)
GUG 28.1(1143534)  GCG  7.4(299495)   GAG 39.6(1609975)  GGG 16.5(669768)
```

Coding GC 52.27% 1st letter GC 55.72% 2nd letter GC 42.54% 3rd letter GC 58.55%

Figure 2

SEQ ID NO:1

```
ATGCTGAGAGCCAAAAACCAGCTGTTCCTGCTGAGCCCCCACTATCTGAGACAGGTCAAAGAAAGTTCCG
GGAGTAGACTGATCCAGCAGAGACTGCTGCACCAGCAGCAGCCACTGCATCCTGAGTGGGCCGCTCTGGC
CAAGAAACAGCTGAAGGGCAAAAACCCAGAAGACCTGATCTGGCACACTCCAGAGGGGATTTCAATCAAG
CCCCTGTACAGCAAAAGGGACACTATGGATCTGCCAGAGGAACTGCCAGGAGTGAAGCCTTTCACCCGCG
GACCTTACCCAACTATGTATACCTTTCGACCCTGGACCAATTCGGCAGTACGCCGGCTTCAGTACTGTGGA
GGAATCAAACAAGTTTTATAAGGACAACATCAAGGCTGGACAGCAGGGCCTGAGTGTGGCATTCGATCTG
GCCACACATCGCGGCTATGACTCAGATAATCCCAGAGTCAGGGGGGACGTGGGAATGGCAGGAGTCGCTA
TCGACACAGTGGAAGATACTAAGATTCTGTTCGATGGAATCCCTCTGGAGAAAATGTCTGTGAGTATGAC
AATGAACGGCGCTGTCATTCCCGTGCTGGCAAACTTCATCGTCACTGGCGAGGAACAGGGGGTGCCTAAG
GAAAAACTGACCGGCACAATTCAGAACGACATCCTGAAGGAGTTCATGGTGCGGAATACTTACATTTTTC
CCCCTGAACCATCCATGAAAATCATTGCCGATATCTTCGAGTACACCGCTAAGCACATGCCCAAGTTCAA
CTCAATTAGCATCTCCGGGTATCATATGCAGGAAGCAGGAGCCGACGCTATTCTGGAGCTGGCTTACACC
CTGGCAGATGGCCTGGAATATTCTCGAACCGGACTGCAGGCAGGCCTGACAATCGACGAGTTCGCTCCTA
GACTGAGTTTCTTTTGGGGAATTGGCATGAACTTTTACATGGAGATCGCCAAGATGAGGGCTGGCCGGAG
ACTGTGGGCACACCTGATCGAGAAGATGTTCCAGCCTAAGAACTCTAAGAGTCTGCTGCTGCGGGCCCAT
TGCCAGACATCCGGCTGGTCTCTGACTGAACAGGACCCATATAACAATATTGTCAGAACCGCAATCGAGG
CAATGGCAGCCGTGTTCGGAGGAACCCAGAGCCTGCACACAAACTCCTTTGATGAGGCCCTGGGGCTGCC
TACCGTGAAGTCTGCTAGGATTGCACGCAATACACAGATCATTATCCAGGAGGAATCCGGAATCCCAAAG
GTGGCCGATCCCTGGGGAGGCTCTTACATGATGGAGTGCCTGACAAACGACGTGTATGATGCTGCACTGA
AGCTGATTAATGAAATCGAGGAAATGGGGGGAATGGCAAAGGCCGTGGCTGAGGGCATTCCAAAACTGAG
GATCGAGGAATGTGCAGCTAGGCGCCAGGCACGAATTGACTCAGGAAGCGAAGTGATCGTCGGGGTGAAT
AAGTACCAGCTGGAGAAAGAAGACGCAGTCGAAGTGCTGGCCATCGATAACACAAGCGTGCGCAATCGAC
AGATTGAGAAGCTGAAGAAAATCAAAAGCTCCCGCGATCAGGCACTGGCCGAACGATGCCTGGCAGCCCT
GACTGAGTGTGCTGCAAGCGGGGACGGAAACATTCTGGCTCTGGCAGTCGATGCCTCCCGGGCTAGATGC
ACTGTGGGGGAAATCACCGACGCCCTGAAGAAAGTCTTCGGAGAGCACAAGGCCAATGATCGGATGGTGA
GCGGCGCTTATAGACAGGAGTTCGGGGAATCTAAAGAGATTACCAGTGCCATCAAGAGGGTGCACAAGTT
CATGGAGAGAGAAGGGCGACGGCCCAGGCTGCTGGTGGCAAAGATGGGACAGGACGGACATGATCGCGGA
GCAAAAGTCATTGCCACCGGGTTCGCTGACCTGGGATTTGACGTGGATATCGGCCCTCTGTTCCAGACAC
CACGAGAGGTCGCACAGCAGGCAGTCGACGCTGATGTGCACGCAGTCGGAGTGTCCACTCTGGCAGCTGG
CCATAAGACCCTGGTGCCTGAACTGATCAAAGAGCTGAACTCTCTGGGCAGACCAGACATCCTGGTCATG
TGCGGCGGCGTGATCCCACCCCAGGATTACGAATTCCTGTTTGAGGTCGGGGTGAGCAACGTGTTCGGAC
CAGGAACCAGGATCCCTAAGGCCGCAGTGCAGGTCCTGGATGATATTGAAAAGTGTCTGGAAAAGAAACA
GCAGTCAGTGTAA
```

Figure 3

SEQ ID NO:2

```
  1 mlraknqlfl lsphylrqvk essgsrliqq rlihqqqplh pewaalakkq lkgknpedli
 61 whtpegisik plyskrdtmd lpeelpgvkp ftrgpyptmy tfrpwtirqy agfstveesn
121 kfykdnikag qqglsvafdl athrgydsdn prvrgdvgma gvaidtvedt kilfdgiple
181 kmsvsmtmng avipvlanfi vtqeeqgvpk ekltgtiqnd ilkefmvrnt yifppepsmk
241 iiadifeyta khmpkfnsis isgyhmqeag adailelayt ladgleysrt glqagltide
301 faprlsffwg igmnfymeia kmragrrlwa hliekmfqpk nsksillrah cqtsgwslte
361 qdpynnivrt aieamaavfg gtqslhtnsf dealglptvk sariarntqi iiqeesgipk
421 vadpwggsym mecltndvyd aalklineie emggmakava egipklriee caarrqarid
481 sgsevivgvn kyqlekedav evlaidntsv rnrqieklkk ikssrdqala ehclaaltec
541 aasgdgnila lavdasrarc tvgeitdalk kvfgehkand rmvsgayrqe fgeskeitsa
601 ikrvhkfmer egrrprllva kmgqdghdrg akviatgfad lqfdvdigpl fqtprevaqq
661 avdadvhavg vstlaaghkt lvpelikeln slgrpdilvm cggvippqdy eflfevgvsn
721 vfgpgtripk aavqvlddie kclekkqqsv
```

SEQ ID NO:3

```
ATGTTAAGAGCTAAGAATCAGCTTTTTTTACTTTCACCTCATTACCTGAGGCAGGTAAAAGAATCATCAG
GCTCCAGGCTCATACAGCAACGACTTCTACACCAGCAACAGCCCCTTCACCCAGAATGGGCTGCCCTGGC
TAAAAAGCAGCTGAAAGGCAAAAACCCAGAAGACCTAATATGGCACACCCCGGAAGGGATCTCTATAAAA
CCCTTGTATTCCAAGAGAGATACTATGGACTTACCTGAAGAACTTCCAGGAGTGAAGCCATTCACACGTG
GACCATATCCTACCATGTATACCTTTAGGCCCTGGACCATCCGCCAGTATGCTGGTTTTAGTACTGTGGA
AGAAAGCAATAAGTTCTATAAGGACAACATTAAGGCTGGTCAGCAGGGATTATCAGTTGCCTTTGATCTG
GCGACACATCGTGGCTATGATTCAGACAACCCTCGAGTTCGTGGTGATGTTGGAATGGCTGGAGTTGCTA
TTGACACTGTGGAAGATACCAAAATTCTTTTTGATGGAATTCCTTTAGAAAAAATGTCAGTTTCCATGAC
TATGAATGGAGCAGTTATTCCAGTTCTTGCAAATTTTATAGTAACTGGAGAAGAACAAGGTGTACCTAAA
GAGAAGCTTACTGGTACCATCCAAAATGATATACTAAAGGAATTTATGGTTCGAAATACATACATTTTTC
CTCCAGAACCATCCATGAAAATTATTGCTGACATTTGAATATACAGCAAACATGCCAAAATTTAA
TTCAATTTCAATTAGTGGATACCATATGCAGGAAGCAGGGGCTGATGCCATTCTGGAGCTGGCCTATACT
TTAGCAGATGGATTGGAGTACTCTAGAACTGGACTCCAGGCTGGCCTGACAATTGATGAATTTGCACCAA
GGTTGTCTTTCTTCTGGGGAATTGGAATGAATTTCTATATGGAAATAGCAAAGATGAGAGCTGGTAGAAG
ACTCTGGGCTCACTTAATAGAGAAAATGTTTCAGCCTAAAAACTCAAAATCTCTTCTTCTAAGAGCACAC
TGTCAGACATCTGGATGGTCACTTACTGAGCAGGATCCCTACAATAATATTGTCCGTACTGCAATAGAAG
CAATGGCAGCAGTATTTGGAGGGACTCAGTCTTTGCACACAAATTCTTTTGATGAAGCTTTGGGTTTGCC
AACTGTGAAAAGTGCTCGAATTGCCAGGAACACACAAATCATCATTCAAGAAGAATCTGGGATTCCCAAA
GTGGCTGATCCTTGGGGAGGTTCTTACATGATGGAATGTCTCACAAATGATGTTTATGATGCTGCTTTAA
AGCTCATTAATGAAATTGAAGAAATGGGTGGAATGGCCAAAGCTGTAGCTGAGGGATAACCTAAACTTCG
AATTGAAGAATGTGCGCCCGAAGACAAGCTAGAATAGAATTCTGGTTCTGAAGTAATTGTTGGAGTAAAT
AAGTACCAGTTGGAAAAAGAAGACGCTGTAGAAGTTCTGGCAATTGATAATACTTCAGTGCGAAACAGGC
AGATTGAAAAACTTAAGAAGATCAAATCCAGCAGGGATCAAGCTTTGGCTGAACGTTGTCTTGCTGCACT
AACCGAATGTGCTGCTAGCGGAGATGGAAATATCCTGGCTCTTGCAGTGGATGCATCTCGGGCAAGATGT
ACAGTGGGAGAAATCACAGATGCCCTGAAAAAGGTATTTGGTGAACATAAAGCGAATGATCGAATGGTGA
GTGGAGCATATCGCCAGGAATTTGGAGAAAGTAAAGAGATAACATCTGCTATCAAGAGGGTTCATAAATT
CATGGAACGTGAAGGTCGCAGACCTCGTCTTCTTGTAGCAAAAATGGGACAAGATGGCCATGACAGAGGA
GCAAAAGTTATTGCTACAGGATTTGCTGATCTTGGTTTGATGTGGACATAGGCCCTCTTTTCCAGACTC
CTCGTGAAGTGGCCCAGCAGGCTGTGGATGCGGATGTGCATGCTGTGGGCATAAGCACCCTCGCTGCTGG
TCATAAAACCCTAGTTCCTGAACTCATCAAAGAACTTAACTCCCTTGGACGGCCAGATATTCTTGTCATG
TGTGGAGGGGTGATACCACCTCAGGATTATGAATTTCTGTTTGAAGTTGGTGTTTCCAATGTATTTGGTC
CTGGGACTCGAATTCCAAAGGCTGCCGTTCAGGTGCTTGATGATATTGAGAAGTGTTTGGAAAAGAAGCA
GCAATCTGTATAA
```

Figure 4

```
Query: synMUT
Subject: MUT (NCBI Reference Sequence: NM_000255.3)

Alignment statistics for match #1
Score                Expect       Identities              Gaps              Strand
1665 bits(1846)      0.0          1721/2253(76%)          0/2253(0%)        Plus/Plus
Query   1    ATGCTGAGAGCCAAAAACCAGCTGTTCCTGCTGAGCCCCACTATCTGAGACAGGTCAAA    60
             ||| | ||||| || || ||||| || | ||     || || ||||| ||||| |||
Sbjct   1    ATGTTAAGAGCTAAGAATCAGCTTTTTTTACTTTCACCTCATTACCTGAGGCAGGTAAAA   60

Query   61   GAAAGTTCCGGGAGTAGACTGATCCAGCAGAGACTGCTGCACCAGCAGCAGCCACTGCAT   120
             |||   || ||    || || || ||||| |||| || ||||||||| ||||| || ||
Sbjct   61   GAATCATCAGGCTCCAGGCTCATACAGCAACGACTTCTACACCAGCAACAGCCCCTTCAC   120

Query   121  CCTGAGTGGGCCGCTCTGGCCAAGAAACAGCTGAAGGGCAAAAACCCAGAAGACCTGATC   180
             || || ||||| || ||||| || || |||||||| |||||||||||||||||||| ||
Sbjct   121  CCAGAATGGGCTGCCCTGGCTAAAAAGCAGCTGAAAGGCAAAAACCCAGAAGACCTAATA   180

Query   181  TGGCACACTCCAGAGGGGATTTCAATCAAGCCCTGTACAGCAAAAGGGACACTATGGAT   240
             |||||||| || || ||||| || || ||| |||    ||| || || ||||||||
Sbjct   181  TGGCACACCCCGGAAGGGATCTCTATAAAACCCTTGTATTCCAAGAGAGATACTATGGAC   240

Query   241  CTGCCAGAGGAACTGCCAGGAGTGAAGCCTTTCACCCGCGGACCTTACCCAACTATGTAT   300
              | || || ||||| |||||||||||||||||| ||||| || ||||| || ||||||
Sbjct   241  TTACCTGAAGAACTTCCAGGAGTGAAGCCATTCACACGTGGACCATATCCTACCATGTAT   300

Query   301  ACCTTTCGACCCTGGACAATTCGGCAGTACGCCGGCTTCAGTACTGTGGAGGAATCAAAC   360
             ||||||   ||||||||  || || |||| || ||  || ||||||||||| |    ||
Sbjct   301  ACCTTTAGGCCCTGGACCATCCGCCAGTATGCTGGTTTTAGTACTGTGGAAGAAAGCAAT   360

Query   361  AAGTTTTATAAGGACAACATCAAGGCTGGACAGCAGGGCCTGAGTGTGGCATTCGATCTG   420
             ||||| ||||| ||||||||| ||||||| |||||||| | |||||||| ||||||||
Sbjct   361  AAGTTCTATAAGGACAACATTAAGGCTGGTCAGCAGGGATTATCAGTTGCCTTTGATCTG   420

Query   421  GCCACACATCGCGGCTATGACTCAGATAATCCCAGAGTCAGGGGGGACGTGGGAATGGCA   480
             || |||||||| ||||||||  ||| |||   || | || || || || ||||||||
Sbjct   421  GCGACACATCGTGGCTATGATTCAGACAACCCTCGAGTTCGTGGTGATGTTGGAATGGCT   480

Query   481  GGAGTCGCTATCGACACAGTGGAAGATACTAAGATTCTGTTCGATGGAATCCCTCTGGAG   540
             ||||| |||| || || |||||||||| || ||||| || ||||||||| |||| | |
Sbjct   481  GGAGTTGCTATTGACACTGTGGAAGATACCAAAATTCTTTTTGATGGAATTCCTTTAGAA   540

Query   541  AAAATGTCTGTGAGTATGACAATGAACGGCGCTGTCATTCCCGTGCTGGCAAACTTCATC   600
             |||||||| ||     ||||| ||||| || ||  || ||||| || || |||| ||
Sbjct   541  AAAATGTCAGTTTCCATGACTATGAATGGAGCAGTTATTCCAGTTCTTGCAAATTTTATA   600

Query   601  GTCACTGGCGAGGAACAGGGGGTGCCTAAGGAAAAACTGACCGGCACAATTCAGAACGAC   660
             || ||||| || |||||  || || || |||| || ||||  || || || || || |
Sbjct   601  GTAACTGGAGAAGAACAAGGTGTACCTAAAGAGAAGCTTACTGGTACCATCCAAAATGAT   660

Query   661  ATCCTGAAGGAGTTCATGGTGCGGAATACTTACATTTTTCCCCCTGAACCATCCATGAAA   720
             || || ||||| || |||||| ||||| |||||||||| |||  || |||||||||||
Sbjct   661  ATACTAAAGGAATTTATGGTTCGAAATACATACATTTTTCCTCCAGAACCATCCATGAAA   720

Query   721  ATCATTGCCGATATCTTCGAGTACACCGCTAAGCACATGCCCAAGTTCAACTCAATTAGC   780
             || || || ||||| |||||||||| || ||||||||||| ||| | |||| ||||
Sbjct   721  ATTATTGCTGACATATTTGAATATACAGCAAAGCACATGCCAAAATTTAATTCAATTTCA   780
```

Figure 4 (continued)

```
Query  781   ATCTCCGGGTATCATATGCAGGAAGCAGGAGCCGACGCTATTCTGGAGCTGGCTTACACC  840
             ||    || || |||||||||||||||  || || || ||||||||||||| || ||
Sbjct  781   ATTAGTGGATACCATATGCAGGAAGCAGGGGCTGATGCCATTCTGGAGCTGGCCTATACT  840

Query  841   CTGGCAGATGGCCTGGAATATTCTCGAACCGGACTGCAGGCAGGCCTGACAATCGACGAG  900
             | ||||||||  ||||  || ||| |||| |||||  |||||||||||||| || ||
Sbjct  841   TTAGCAGATGGATTGGAGTACTCTAGAACTGGACTCCAGGCTGGCCTGACAATTGATGAA  900

Query  901   TTCGCTCCTAGACTGAGTTTCTTTTGGGGAATTGGCATGAACTTTTACATGGAGATCGCC  960
             || || || ||  ||  |||||  ||||||||||  ||||| |||| |||||  || ||
Sbjct  901   TTTGCACCAAGGTTGTCTTTCTTCTGGGGAATTGGAATGAATTTCTATATGGAAATAGCA  960

Query  961   AAGATGAGGGCTGGCCGGAGACTGTGGGCACACCTGATCGAGAAGATGTTCCAGCCTAAG  1020
             ||||||||  |||| | ||||||| ||| || ||  ||  | ||||| |||||||||
Sbjct  961   AAGATGAGAGCTGGTAGAAGACTCTGGGCTCACTTAATAGAGAAAATGTTTCAGCCTAAA  1020

Query  1021  AACTCTAAGAGTCTGCTGCTGCGGGCCCATTGCCAGACATCCGGCTGGTCTCTGACTGAA  1080
             ||||| ||   ||| || || | || || || ||||||| || ||||| ||  || |||
Sbjct  1021  AACTCAAAATCTCTTCTTCTAAGAGCACACTGTCAGACATCTGGATGGTCACTTACTGAG  1080

Query  1081  CAGGACCCATATAACAATATTGTCAGAACCGCAATCGAGGCAATGGCAGCCGTGTTCGGA  1140
             ||||| || || || |||||||| ||   || |||| || |||||||||||| || |||
Sbjct  1081  CAGGATCCCTACAATAATATTGTCCGTACTGCAATAGAAGCAATGGCAGCAGTATTTGGA  1140

Query  1141  GGAACCCAGAGCCTGCACACAAACTCCTTTGATGAGGCCCTGGGGCTGCCTACCGTGAAG  1200
             || || |||   ||||||||||| ||  |||||| | ||||| |||||| || ||||
Sbjct  1141  GGGACTCAGTCTTTGCACACAAATTCTTTTGATGAAGCTTTGGGTTTGCCAACTGTGAAA  1200

Query  1201  TCTGCTAGGATTGCACGCAATACACAGATCATTATCCAGGAGGAATCCGGAATCCCAAAG  1260
              ||| ||||| | || |||||||||| ||||| ||  ||||| || ||||||||||||
Sbjct  1201  AGTGCTCGAATTGCCAGGAACACACAAATCATCATTCAAGAAGAATCTGGGATTCCCAAA  1260

Query  1261  GTGGCCGATCCCTGGGGAGGCTCTTACATGATGGAGTGCCTGACAAACGACGTGTATGAT  1320
             ||||| |||||| ||||||| ||||||||||||| || || || |||| || |||||||
Sbjct  1261  GTGGCTGATCCTTGGGGAGGTTCTTACATGATGGAATGTCTCACAAATGATGTTTATGAT  1320

Query  1321  GCTGCACTGAAGCTGATTAATGAAATCGAGGAAATGGGGGGAATGGCAAAGGCCGTGGCT  1380
             ||||| || ||||| ||||||||| || |||||||||| |||||||||||| || |||
Sbjct  1321  GCTGCTTTAAAGCTCATTAATGAAATTGAAGAAATGGGTGGAATGGCCAAAGCTGTAGCT  1380

Query  1381  GAGGGCATTCCAAAACTGAGGATCGAGGAATGTGCAGCTAGGCGCCAGGCACGAATTGAC  1440
             |||||  ||  || ||||| ||  || ||||||||| |   |   | || ||| || ||
Sbjct  1381  GAGGGAATACCTAAACTTCGAATTGAAGAATGTGCTGCCCGAAGACAAGCTAGAATAGAT  1440

Query  1441  TCAGGAAGCGAAGTGATCGTCGGGGTGAATAAGTACCAGCTGGAGAAAGAAGACGCAGTC  1500
             || ||     ||||| || || || ||||||||||||| |||||||||||||||| |||
Sbjct  1441  TCTGGTTCTGAAGTAATTGTTGGAGTAAATAAGTACCAGTTGGAAAAGAAGACGCTGTA  1500

Query  1501  GAAGTGCTGGCCATCGATAACACAAGCGTGCGCAATCGACAGATTGAGAAGCTGAAGAAA  1560
             ||||| ||||| || || || || ||    || || | |||||||| |||| ||||||
Sbjct  1501  GAAGTTCTGGCAATTGATAATACTTCAGTGCGAAACAGGCAGATTGAAAAACTTAAGAAG  1560

Query  1561  ATCAAAAGCTCCCGCGATCAGGCACTGGCCGAACGATGCCTGGCAGCCCTGACTGAGTGT  1620
             ||||| |   | |  |||||  |  |||| |||| | ||| |||||| || ||| ||||
Sbjct  1561  ATCAAATCCAGCAGGGATCAAGCTTTGGCTGAACGTTGTCTTGCTGCACTAACCGAATGT  1620

Query  1621  GCTGCAAGCGGGGACGGAAACATTCTGGCTCTGGCAGTCGATGCCTCCCGGGCTAGATGC  1680
             ||||| ||||| || |||||| || |||||| |||||  |||| ||  ||||| |||||
Sbjct  1621  GCTGCTAGCGGAGATGGAAATATCCTGGCTCTTGCAGTGGATGCATCTCGGGCAAGATGT  1680
```

Figure 4 (continued)

```
Query  1681  ACTGTGGGGGAAATCACCGACGCCCTGAAGAAAGTCTTCGGAGAGCACAAGGCCAATGAT  1740
             ||  |||||  ||||||||  ||  ||||||||  ||  ||  ||  ||  ||  ||  ||||||
Sbjct  1681  ACAGTGGGAGAAATCACAGATGCCCTGAAAAAGGTATTTGGTGAACATAAAGCGAATGAT  1740

Query  1741  CGGATGGTGAGCGGCGCTTATAGACAGGAGTTCGGGGAATCTAAAGAGATTACCAGTGCC  1800
             ||  ||||||||  ||  |||  |  |||||  ||  ||  |||  ||||||||||  ||  |||
Sbjct  1741  CGAATGGTGAGTGGAGCATATCGCCAGGAATTTGGAGAAAGTAAAGAGATAACATCTGCT  1800

Query  1801  ATCAAGAGGGTGCACAAGTTCATGGAGAGAGAAGGGCGACGGCCCAGGCTGCTGGTGGCA  1860
             ||||||||||  ||  ||  ||||||||  |  |||||  ||  |  ||  |  ||  ||  |||
Sbjct  1801  ATCAAGAGGGTTCATAAATTCATGGAACGTGAAGGTCGCAGACCTCGTCTTCTTGTAGCA  1860

Query  1861  AAGATGGGACAGGACGGACATGATCGCGGAGCAAAAGTCATTGCCACCGGGTTCGCTGAC  1920
             ||  ||||||||  ||  ||  |||||  |  ||||||||||||  |||||  ||  ||  |||||
Sbjct  1861  AAAATGGGACAAGATGGCCATGACAGAGGAGCAAAAGTTATTGCTACAGGATTTGCTGAT  1920

Query  1921  CTGGGATTTGACGTGGATATCGGCCCTCTGTTCCAGACACCACGAGAGGTCGCACAGCAG  1980
             ||  ||  |||||  |||||  ||  ||||||||  |||||||||  ||  ||  ||  ||||||
Sbjct  1921  CTTGGTTTTGATGTGGACATAGGCCCTCTTTTCCAGACTCCTCGTGAAGTGGCCCAGCAG  1980

Query  1981  GCAGTCGACGCTGATGTGCACGCAGTCGGAGTGTCCACTCTGGCAGCTGGCCATAAGACC  2040
             ||  ||  ||  ||  |||||||||  ||  ||  ||  |  |||  ||  ||  |||||  |||||  |||
Sbjct  1981  GCTGTGGATGCGGATGTGCATGCTGTGGGCATAAGCACCCTCGCTGCTGGTCATAAAACC  2040

Query  2041  CTGGTGCCTGAACTGATCAAAGAGCTGAACTCTCTGGGCAGACCAGACATCCTGGTCATG  2100
             ||  ||  ||||||||||  ||||||||  ||  |||||  ||  ||  |  |||||  ||  ||  ||||||
Sbjct  2041  CTAGTTCCTGAACTCATCAAAGAACTTAACTCCCTTGACGGCCAGATATTCTTGTCATG  2100

Query  2101  TGCGGCGGCGTGATCCCACCCCAGGATTACGAATTCCTGTTTGAGGTCGGGGTGAGCAAC  2160
             ||  ||  ||  |||||  |||||  |||||||||  |||||  |||||||  ||  ||  |||
Sbjct  2101  TGTGGAGGGGTGATACCACCTCAGGATTATGAATTTCTGTTTGAAGTTGGTGTTCCAAT  2160

Query  2161  GTGTTCGGACCAGGAACCAGGATCCCTAAGGCCGCAGTGCAGGTCCTGGATGATATTGAA  2220
             ||  ||  ||  ||  ||  ||  |  ||  ||  ||||  ||  ||  |||||  ||  ||||||||||
Sbjct  2161  GTATTTGGTCCTGGGACTCGAATTCCAAAGGCTGCCGTTCAGGTGCTTGATGATATTGAG  2220

Query  2221  AAGTGTCTGGAAAAGAAACAGCAGTCAGTGTAA  2253
             ||||||  ||||||||||  |||||||  ||  ||  |||
Sbjct  2221  AAGTGTTTGGAAAAGAAGCAGCAATCTGTATAA  2253
```

Figure 5

```
ATG  CTG  AGA  GCC  AAA  AAC  CAG  CTG  TTC  CTG  CTG  AGC  CCC  CAC
 M    L    R    A    K    N    Q    L    F    L    L    S    P    H

TAT  CTG  AGA  CAG  GTC  AAA  GAA  AGT  TCC  GGG  AGT  AGA  CTG  ATC
               1
 Y    L    R    Q    V    K    E    S    S    G    S    R    L    I

CAG  CAG  AGA  CTG  CTG  CAC  CAG  CAG  CAG  CCA  CTG  CAT  CCT  GAG
 Q    Q    R    L    L    H    Q    Q    Q    P    L    H    P    E

TGG  GCC  GCT  CTG  GCC  AAG  AAA  CAG  CTG  AAG  GGC  AAA  AAC  CCA
                                   1
 W    A    A    L    A    K    K    Q    L    K    G    K    N    P

GAA  GAC  CTG  ATC  TGG  CAC  ACT  CCA  GAG  GGG  ATT  TCA  ATC  AAG
                                                             1
 E    D    L    I    W    H    T    P    E    G    I    S    I    K

CCC  CTG  TAC  AGC  AAA  AGG  GAC  ACT  ATG  GAT  CTG  CCA  GAG  GAA
                                                   1
 P    L    Y    S    K    R    D    T    M    D    L    P    E    E

CTG  CCA  GGA  GTG  AAG  CCT  TTC  ACC  CGC  GGA  CCT  TAC  CCA  ACT
                                                   2
                                                   1
 L    P    G    V    K    P    F    T    R    G    P    Y    P    T

ATG  TAT  ACC  TTT  CGA  CCC  TGG  ACA  ATT  CGG  CAG  TAC  GCC  GGC
                                                   1
 M    Y    T    F    R    P    W    T    I    R    Q    Y    A    G

TTC  AGT  ACT  GTG  GAG  GAA  TCA  AAC  AAG  TTT  TAT  AAG  GAC  AAC
                                             1
 F    S    T    V    E    E    S    N    K    F    Y    K    D    N

ATC  AAG  GCT  GGA  CAG  CAG  GGC  CTG  AGT  GTG  GCA  TTC  GAT  CTG
               1
 I    K    A    G    Q    Q    G    L    S    V    A    F    D    L

GCC  ACA  CAT  CGC  GGC  TAT  GAC  TCA  GAT  AAT  CCC  AGA  GTC  AGG
 A    T    H    R    G    Y    D    S    D    N    P    R    V    R

GGG  GAC  GTG  GGA  ATG  GCA  GGA  GTC  GCT  ATC  GAC  ACA  GTG  GAA
 G    D    V    G    M    A    G    V    A    I    D    T    V    E

GAT  ACT  AAG  ATT  CTG  TTC  GAT  GGA  ATC  CCT  CTG  GAG  AAA  ATG
 D    T    K    I    L    F    D    G    I    P    L    E    K    M
```

Figure 5 (continued)

| TCT | GTG | AGT | ATG | ACA | ATG | AAC | GGC | GCT | GTC | ATT | CCC | GTG | CTG |
|---|---|---|---|---|---|---|---|---|---|---|---|---|---|
|   |   |   | 1 |   |   | 1 |   |   |   |   |   |   |   |
| S | V | S | M | T | M | N | G | A | V | I | P | V | L |

| GCA | AAC | TTC | ATC | GTC | ACT | GGC | GAG | GAA | CAG | GGG | GTG | CCT | AAG |
|---|---|---|---|---|---|---|---|---|---|---|---|---|---|
|   |   |   |   |   |   |   |   |   |   | 1 |   |   |   |
| A | N | F | I | V | T | G | E | E | Q | G | V | P | K |

| GAA | AAA | CTG | ACC | GGC | ACA | ATT | CAG | AAC | GAC | ATC | CTG | AAG | GAG |
|---|---|---|---|---|---|---|---|---|---|---|---|---|---|
|   | 1 |   |   |   |   |   |   |   |   |   |   |   |   |
| E | K | L | T | G | T | I | Q | N | D | I | L | K | E |

| TTC | ATG | GTG | CGG | AAT | ACT | TAC | ATT | TTT | CCC | CCT | GAA | CCA | TCC |
|---|---|---|---|---|---|---|---|---|---|---|---|---|---|
|   |   |   |   |   |   |   |   |   |   |   |   | 1 |   |
| F | M | V | R | N | T | Y | I | F | P | P | E | P | S |

| ATG | AAA | ATC | ATT | GCC | GAT | ATC | TTC | GAG | TAC | ACC | GCT | AAG | CAC |
|---|---|---|---|---|---|---|---|---|---|---|---|---|---|
|   |   | 1 |   |   |   |   |   |   |   |   |   |   | 1 |
| M | K | I | I | A | D | I | F | E | Y | T | A | K | H |

| ATG | CCC | AAG | TTC | AAC | TCA | ATT | AGC | ATC | TCC | GGG | TAT | CAT | ATG |
|---|---|---|---|---|---|---|---|---|---|---|---|---|---|
|   |   |   |   |   |   |   | 1 |   |   |   |   |   |   |
| M | P | K | F | N | S | I | S | I | S | G | Y | H | M |

| CAG | GAA | GCA | GGA | GCC | GAC | GCT | ATT | CTG | GAG | CTG | GCT | TAC | ACC |
|---|---|---|---|---|---|---|---|---|---|---|---|---|---|
|   |   |   |   |   |   |   |   |   |   |   |   | 1 |   |
| Q | E | A | G | A | D | A | I | L | E | L | A | Y | T |

| CTG | GCA | GAT | GGC | CTG | GAA | TAT | TCT | CGA | ACC | GGA | CTG | CAG | GCA |
|---|---|---|---|---|---|---|---|---|---|---|---|---|---|
|   |   |   |   |   |   |   |   |   |   |   |   | 1 |   |
| L | A | D | G | L | E | Y | S | R | T | G | L | Q | A |

| GGC | CTG | ACA | ATC | GAC | GAG | TTC | GCT | CCT | AGA | CTG | AGT | TTC | TTT |
|---|---|---|---|---|---|---|---|---|---|---|---|---|---|
| G | L | T | I | D | E | F | A | P | R | L | S | F | F |

| TGG | GGA | ATT | GGC | ATG | AAC | TTT | TAC | ATG | GAG | ATC | GCC | AAG | ATG |
|---|---|---|---|---|---|---|---|---|---|---|---|---|---|
| W | G | I | G | M | N | F | Y | M | E | I | A | K | M |

| AGG | GCT | GGC | CGG | AGA | CTG | TGG | GCA | CAC | CTG | ATC | GAG | AAG | ATG |
|---|---|---|---|---|---|---|---|---|---|---|---|---|---|
|   |   |   |   |   |   |   |   |   |   |   |   |   | 1 |
| R | A | G | R | R | L | W | A | H | L | I | E | K | M |

| TTC | CAG | CCT | AAG | AAC | TCT | AAG | AGT | CTG | CTG | CTG | CGG | GCC | CAT |
|---|---|---|---|---|---|---|---|---|---|---|---|---|---|
|   |   |   |   |   |   |   |   |   | 1 |   |   |   |   |
| F | Q | P | K | N | S | K | S | L | L | L | R | A | H |

| TGC | CAG | ACA | TCC | GGC | TGG | TCT | CTG | ACT | GAA | CAG | GAC | CCA | TAT |
|---|---|---|---|---|---|---|---|---|---|---|---|---|---|
| C | Q | T | S | G | W | S | L | T | E | Q | D | P | Y |

Figure 5 (continued)

| AAC | AAT | ATT | GTC | AGA | ACC | GCA | ATC | GAG | GCA | ATG | GCA | GCC | GTG |
|---|---|---|---|---|---|---|---|---|---|---|---|---|---|
|  |  |  |  |  | 1 |  | 1 |  |  | 1 |  |  |  |
| N | N | I | V | R | T | A | I | E | A | M | A | A | V |

| TTC | GGA | GGA | ACC | CAG | AGC | CTG | CAC | ACA | AAC | TCC | TTT | GAT | GAG |
|---|---|---|---|---|---|---|---|---|---|---|---|---|---|
| F | G | G | T | Q | S | L | H | T | N | S | F | D | E |

| GCC | CTG | GGG | CTG | CCT | ACC | GTG | AAG | TCT | GCT | AGG | ATT | GCA | CGC |
|---|---|---|---|---|---|---|---|---|---|---|---|---|---|
|  |  |  |  |  |  |  |  |  | 1 |  |  |  |  |
| A | L | G | L | P | T | V | K | S | A | R | I | A | R |

| AAT | ACA | CAG | ATC | ATT | ATC | CAG | GAG | GAA | TCC | GGA | ATC | CCA | AAG |
|---|---|---|---|---|---|---|---|---|---|---|---|---|---|
| N | T | Q | I | I | I | Q | E | E | S | G | I | P | K |

| GTG | GCC | GAT | CCC | TGG | GGA | GGC | TCT | TAC | ATG | ATG | GAG | TGC | CTG |
|---|---|---|---|---|---|---|---|---|---|---|---|---|---|
|  |  |  | 1 |  |  |  |  |  |  |  |  | 1 |  |
| V | A | D | P | W | G | G | S | Y | M | M | E | C | L |

| ACA | AAC | GAC | GTG | TAT | GAT | GCT | GCA | CTG | AAG | CTG | ATT | AAT | GAA |
|---|---|---|---|---|---|---|---|---|---|---|---|---|---|
| 1 |  |  |  |  |  |  |  |  |  |  |  |  |  |
| T | N | D | V | Y | D | A | A | L | K | L | I | N | E |

| ATC | GAG | GAA | ATG | GGG | GGA | ATG | GCA | AAG | GCC | GTG | GCT | GAG | GGC |
|---|---|---|---|---|---|---|---|---|---|---|---|---|---|
| I | E | E | M | G | G | M | A | K | A | V | A | E | G |

| ATT | CCA | AAA | CTG | AGG | ATC | GAG | GAA | TGT | GCA | GCT | AGG | CGC | CAG |
|---|---|---|---|---|---|---|---|---|---|---|---|---|---|
|  |  |  |  | 1 | 1 |  |  |  |  | 1 | 1 |  |  |
| I | P | K | L | R | I | E | E | C | A | A | R | R | Q |

| GCA | CGA | ATT | GAC | TCA | GGA | AGC | GAA | GTG | ATC | GTC | GGG | GTG | AAT |
|---|---|---|---|---|---|---|---|---|---|---|---|---|---|
| A | R | I | D | S | G | S | E | V | I | V | G | V | N |

| AAG | TAC | CAG | CTG | GAG | AAA | GAA | GAC | GCA | GTC | GAA | GTG | CTG | GCC |
|---|---|---|---|---|---|---|---|---|---|---|---|---|---|
|  |  |  |  |  |  |  | 1 | 1 |  |  |  |  | 1 |
| K | Y | Q | L | E | K | E | D | A | V | E | V | L | A |

| ATC | GAT | AAC | ACA | AGC | GTG | CGC | AAT | CGA | CAG | ATT | GAG | AAG | CTG |
|---|---|---|---|---|---|---|---|---|---|---|---|---|---|
| I | D | N | T | S | V | R | N | R | Q | I | E | K | L |

| AAG | AAA | ATC | AAA | AGC | TCC | CGC | GAT | CAG | GCA | CTG | GCC | GAA | CGA |
|---|---|---|---|---|---|---|---|---|---|---|---|---|---|
|  | 1 |  | 1 |  | 2 |  |  |  |  |  |  |  | 1 |
| K | K | I | K | S | S | R | D | Q | A | L | A | E | R |

| TGC | CTG | GCA | GCC | CTG | ACT | GAG | TGT | GCT | GCA | AGC | GGG | GAC | GGA |
|---|---|---|---|---|---|---|---|---|---|---|---|---|---|
| 1 |  |  | 1 |  |  |  |  |  |  | 1 | 1 |  |  |
| C | L | A | A | L | T | E | C | A | A | S | G | D | G |

Figure 5 (continued)

| AAC | ATT | CTG | GCT | CTG | GCA | GTC | GAT | GCC | TCC | CGG | GCT | AGA | TGC |
|-----|-----|-----|-----|-----|-----|-----|-----|-----|-----|-----|-----|-----|-----|
| N | I | L | A | L | A | V | D | A | S | R | A | R | C |

| ACT | GTG | GGG | GAA | ATC | ACC | GAC | GCC | CTG | AAG | AAA | GTC | TTC | GGA |
|-----|-----|-----|-----|-----|-----|-----|-----|-----|-----|-----|-----|-----|-----|
| T | V | G | E | I | T | D | A | L | K | K | V | F | G |

GAG CAC AAG GCC(2) AAT GAT CGG ATG GTG AGC GGC GCT TAT AGA(1,2)
E H K A N D R M V S G A Y R

CAG GAG TTC GGG GAA(2) TCT AAA GAG ATT ACC(1) AGT GCC ATC AAG
Q E F G E S K E I T S A I K

AGG GTG CAC AAG TTC ATG GAG AGA GAA GGG CGA(1) CGG CCC AGG
R V H K F M E R E G R R P R

CTG CTG GTG GCA AAG ATG GGA(1) CAG GAC GGA CAT(1) GAT CGC GGA(1)
L L V A K M G Q D G H D R G

GCA AAA GTC ATT GCC ACC GGG TTC GCT GAC CTG GGA TTT GAC
A K V I A T G F A D L G F D

GTG GAT ATC GGC CCT CTG TTC CAG ACA(2) CCA CGA GAG GTC(1) GCA
V D I G P L F Q T P R E V A

CAG CAG GCA GTC GAC GCT(2,1) GAT GTG CAC GCA GTC GGA GTG(1) TCC
Q Q A V D A D V H A V G V S

ACT CTG GCA(2,1) GCT(1) GGC CAT(1) AAG ACC CTG GTG CCT GAA CTG ATC
T L A A G H K T L V P E L I

AAA GAG CTG AAC TCT CTG GGC AGA CCA GAC ATC CTG GTC ATG(1)
K E L N S L G R P D I L V M

TGC GGC(1) GGC GTG ATC CCA CCC CAG GAT TAC GAA TTC CTG TTT
C G G V I P P Q D Y E F L F

GAG GTC GGG GTG AGC AAC GTG TTC GGA CCA GGA ACC AGG ATC
E V G V S N V F G P G T R I

Figure 5 (continued)

| CCT | AAG | GCC | GCA | GTG | CAG | GTC | CTG | GAT | GAT | ATT | GAA | AAG | TGT |
|-----|-----|-----|-----|-----|-----|-----|-----|-----|-----|-----|-----|-----|-----|
|     |     |     | 2   |     |     |     |     |     |     |     | 1   |     |     |
| P   | K   | A   | A   | V   | Q   | V   | L   | D   | D   | I   | E   | K   | C   |

| CTG | GAA | AAG | AAA | CAG | CAG | TCA | GTG | TAA |
|-----|-----|-----|-----|-----|-----|-----|-----|-----|
| L   | E   | K   | K   | Q   | Q   | S   | V   |     |

Adeno-associated Virus *syn*MUT Expression Cassette

ITR=adeno-associated virus inverted terminal repeats
HCR=hepatic control region
hAAT= human alpha-anti-trypsin promoter (liver specific expression)
*synMUT*= synthetic human methylmalonyl-CoA synthetase
Poly-A=polyadenylation signal

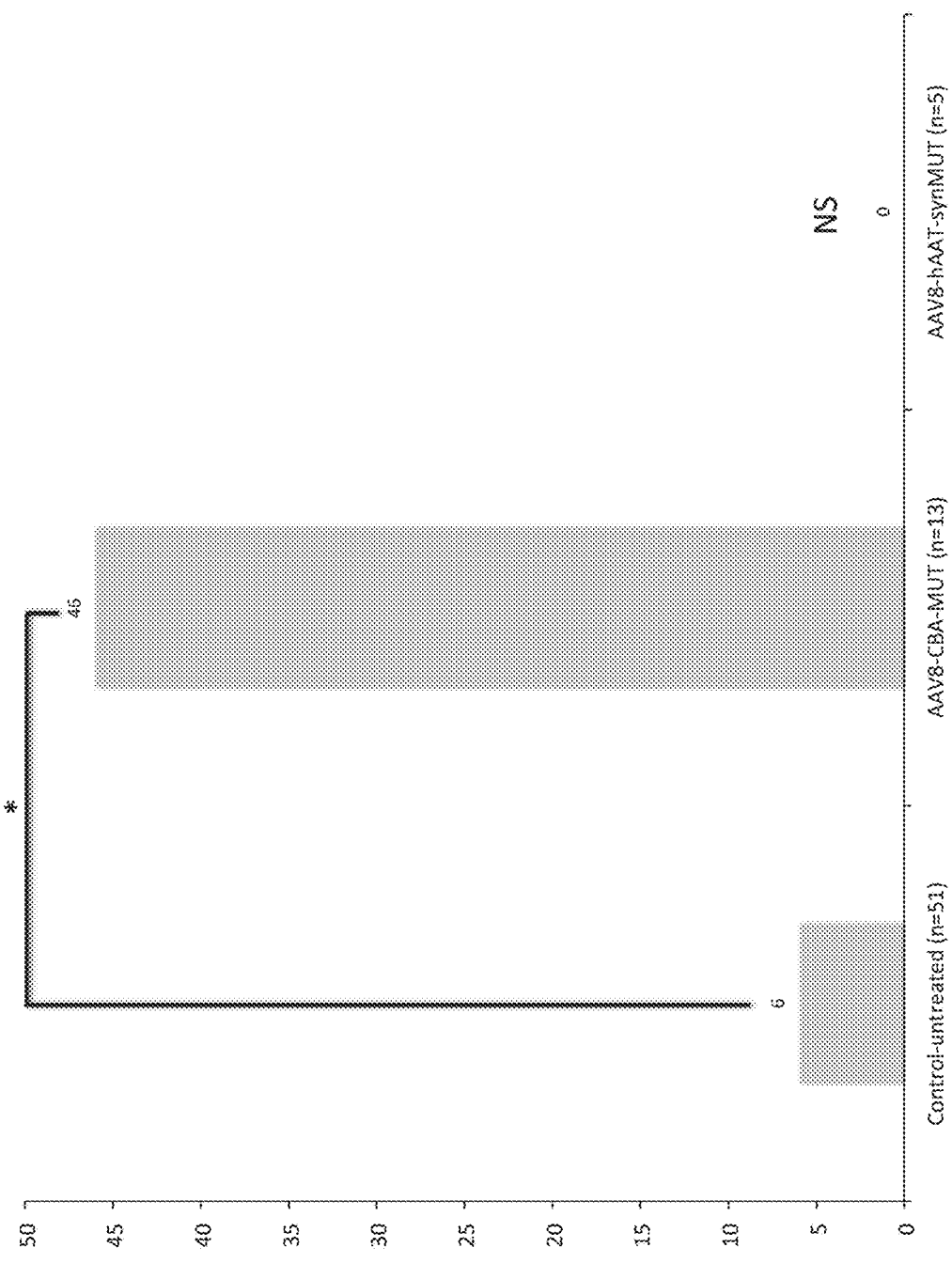

SYNTHETIC METHYLMALONYL-COA MUTASE TRANSGENE FOR THE TREATMENT OF MUT CLASS METHYLMALONIC ACIDEMIA (MMA)

PRIORITY DATA

This application is a continuation of U.S. patent application Ser. No. 14/773,885, filed Sep. 9, 2015, which is a national phase entry pursuant to 35 U.S.C. § 371 of International Patent Application No. PCT/US2014/028045, filed Mar. 14, 2014, which application claims the benefit of U.S. Provisional Application No. 61/792,081, filed Mar. 15, 2013, the entire disclosure of which is hereby incorporated by reference.

STATEMENT OF GOVERNMENT INTEREST

The instant application was made with government support; the government has certain rights in this invention.

SEQUENCE LISTING DATA

The Sequence Listing text document filed herewith, created Feb. 20, 2014, size 13 kilobytes, and named "6137NHGRI6PCT_Sequence_Listing_ST25.txt," is incorporated herein by reference in its entirety.

FIELD OF THE INVENTION

The subject invention relates to engineering of the human methylmalonyl-coA mutase gene so as to enhance its expression in eukaryotic cells. Compared to the natural human MUT gene, the subject synthetic gene sequences (synMUT) are codon-optimized to enhance expression upon administration.

BACKGROUND

Methylmalonic acidemia (MMA) is an autosomal recessive disorder caused by defects in the mitochondrial localized enzyme methylmalonyl-CoA mutase (MUT) (Manoli, et al. 2010 Methylmalonic Acidemia (in *Gene Reviews*, eds. Pagon, et al.)). The estimated incidence of MMA is 1 in 25,000-48,000. MUT is an enzyme that catalyzes the conversion of L-methylmalonyl-CoA to succinyl-CoA. This reaction is one of several enzymatic reactions required to metabolize branch chain amino acids, odd chain fatty acids, and propionate produced by the gut flora (Chandler, et al. 2005 *Mol Genet Metab* 86:34-43). MUT deficiency, the most common cause of MMA, is characterized by the accumulation of methylmalonic acid and other disease-related metabolites. The disease is managed with dietary restriction of amino acid precursors and cofactors but lacks definitive therapy. MMA can lead to metabolic instability, seizures, strokes, and kidney failure, and it can be lethal even when patients are being properly managed, underscoring the need for new therapies for this disease. Even though MMA is rare, all babies born in the USA are screened for this condition as newborns, emphasizing the need to develop better therapies.

SUMMARY

As discussed above, the only treatments for MMA currently available are dietary restrictions. Patients still become metabolically unstable while on diet restriction and experience disease progression, despite medical therapy. These episodes result in numerous hospitalizations and can be fatal. The synthetic human methylmalonyl-CoA mutase (synMUT) transgene can be used as a drug, via viral- or non-viral mediated gene delivery, to restore MUT function in MMA patients, prevent metabolic instability, and ameliorate disease progression. Because this enzyme may also be important in other disorders of branched chain amino acid oxidation, gene delivery of synthetic MUT gene could be used to treat conditions other than MUT MMA.

Additionally, the synMUT transgene can be used for the in vitro production of MUT for use in enzyme replacement therapy for MMA. Enzyme replacement therapy is accomplished by administration of the synthetic MUT protein orally, sub-cutaneously, intra-muscularly, intravenously, or by other therapeutic delivery routes.

Thus, in one aspect, the invention is directed to a synthetic methylmalonyl-CoA mutase (MUT) polynucleotide (synMUT) selected from the group consisting of:
  a) a polynucleotide comprising the nucleic acid sequence of SEQ. ID NO:1;
  b) a polynucleotide having the nucleic acid sequence of SEQ ID NO:1;
  c) a polynucleotide having a nucleic acid sequence with at least about 80% identity to the nucleic acid sequence of SEQ ID NO:1;
  d) a polynucleotide encoding a polypeptide having the amino acid sequence of SEQ ID NO:3 or an amino acid sequence substantially identical to the amino acid sequence of SEQ ID NO:3, wherein the polynucleotide does not have the nucleic acid sequence of SEQ ID NO:3; and
  e) a polynucleotide encoding an active fragment of the methylmalonyl-CoA mutase (MUT) protein, wherein the polynucleotide in its entirety does not share 100% identity with a portion of the nucleic acid sequence of SEQ ID NO:3.

In one embodiment, the fragment includes only amino acid residues 33-750, which is encoded between nucleotides 63-2250 in synMUT, and which represents the active, processed form of MUT.

By active can be meant, for example, the enzyme's ability to catalyze the isomerization of methylmalonyl-CoA to succinyl-CoA. The activity can be assayed using methods well-known in the art (as described in the context of protein function, below).

In one embodiment of a synthetic polynucleotide according to the invention, the nucleic acid sequence encodes a polypeptide having the amino acid sequence of SEQ ID NO:2 or an amino acid sequence with at least about 90% identity to the amino acid sequence of SEQ ID NO:2.

In another embodiment, the synthetic polynucleotide exhibits augmented expression relative to the expression of naturally occurring human methylmalonyl-CoA mutase polynucleotide sequence (SEQ ID NO:3) in a subject. In yet another embodiment, the synthetic polynucleotide having augmented expression comprises a nucleic acid sequence comprising codons that have been optimized relative to the naturally occurring human methylmalonyl-CoA mutase polynucleotide sequence (SEQ ID NO:3). In still another embodiment of a synthetic polynucleotide according to the invention, the nucleic acid sequence has at least about 80% of less commonly used codons replaced with more commonly used codons.

In one embodiment of a synthetic polynucleotide according to the invention, the polynucleotide is a polynucleotide having a nucleic acid sequence with at least about 85% identity to the nucleic acid sequence of SEQ ID NO: 1. In another embodiment, the polynucleotide is a polynucleotide having a nucleic acid sequence with at least about 90% identity to the nucleic acid sequence of SEQ ID NO: 1. In still another embodiment, the polynucleotide is a polynucleotide having a nucleic acid sequence with at least about 95% identity to the nucleic acid sequence of SEQ ID NO:1.

In one embodiment of a synthetic polynucleotide according to the invention, the nucleic acid sequence is a DNA sequence. In another embodiment, the nucleic acid sequence is a RNA sequence or peptide modified nucleic acid sequence. In another embodiment, the synthetic polynucleotide according to the invention encodes an active MUT fragment, amino acids 33-750 of synMUT, corresponding to base pairs 67-2250 in synMUT.

In another aspect, the invention is directed to an expression vector comprising the herein-described synthetic polynucleotide. In another embodiment of a vector according to the invention, the synthetic polynucleotide is operably linked to an expression control sequence. In still another embodiment, the synthetic polynucleotide is codon-optimized.

In a further aspect, the invention is directed to a method of treating a disease or condition mediated by methylmalonyl-CoA mutase or low levels of methylmalonyl-CoA mutase activity, the method comprising administering to a subject the herein-described synthetic polynucleotide.

In still a further aspect, the invention is directed to a method of treating a disease or condition mediated by methylmalonyl-CoA mutase, the method comprising administering to a subject a methylmalonyl-CoA mutase produced using the synthetic polynucleotide described herein. In another embodiment of a method of treatment according to the invention, the disease or condition is methylmalonic acidemia (MMA).

In one aspect, the invention is directed to a composition comprising the synthetic polynucleotide of claim 1 and a pharmaceutically acceptable carrier.

In another aspect, the invention is directed to a transgenic animal whose genome comprises a polynucleotide sequence encoding methylmalonyl-CoA mutase or a functional fragment thereof. In still another aspect, the invention is directed to a method for producing such a transgenic animal, comprising: providing an exogenous expression vector comprising a polynucleotide comprising a promoter operably linked to a polynucleotide encoding methylmalonyl-CoA mutase or a functional fragment thereof; introducing the vector into a fertilized oocyte; and transplanting the oocyte into a female animal.

In one aspect, the invention is directed to a transgenic animal whose genome comprises the synthetic polynucleotide described herein. In another aspect, the invention is directed to a method for producing such a transgenic animal, comprising: providing an exogenous expression vector comprising a polynucleotide comprising a promoter operably linked to the synthetic polynucleotide described herein; introducing the vector into a fertilized oocyte; and transplanting the oocyte into a female animal.

Methods for producing transgenic animals are known in the art and include, without limitation, transforming embryonic stem cells in tissue culture, injecting the transgene into the pronucleus of a fertilized animal egg (DNA microinjection), genetic/genome engineering, viral delivery (for example, retrovirus-mediated gene transfer).

Transgenic animals according to the invention include, without limitation, rodent (mouse, rat, squirrel, guinea pig, hamster, beaver, porcupine), frog, ferret, rabbit, chicken, pig, sheep, goat, cow primate, and the like.

In another aspect, the invention is directed to the preclinical amelioration or rescue from the disease state, for example, methylmalonic acidemia, that the afflicted subject exhibits. This may include symptoms, such as lethargy, lethality, metabolic acidosis, and biochemical perturbations, such as increased levels of methylmalonic acid in blood, urine, and body fluids.

In still another aspect, the invention is directed to a method for producing a genetically engineered animal as a source of recombinant synMUT. In another aspect, genome editing, or genome editing with engineered nucleases (GEEN) may be performed with the synMUT nucleotides of the present invention allowing synMUT DNA to be inserted, replaced, or removed from a genome using artificially engineered nucleases. Any known engineered nuclease may be used such as Zinc finger nucleases (ZFNs), Transcription Activator-Like Effector Nucleases (TALENs), the CRISPR/Cas system, and engineered meganuclease re-engineered homing endonucleases. Alternately, the nucleotides of the present invention including synMUT, in combination with a CASP/CRISPR, ZFN, or TALEN can be used to engineer correction at the locus in a patient's cell either in vivo or ex vivo, then, in one embodiment, use that corrected cell, such as a fibroblast or lymphoblast, to create an iPS or other stem cell for use in cellular therapy.

BRIEF DESCRIPTION OF THE DRAWINGS

FIG. 1 illustrates the list of codon frequencies in the human proteome.

FIG. 2 illustrates a codon-optimized synMUT (SEQ ID NO:1) of the subject invention.

FIG. 3 illustrates naturally occurring *Homo sapiens* MUT amino acid sequence (SEQ ID NO:2) and naturally occurring *Homo sapiens* MUT gene (SEQ ID NO:3).

FIG. 4 illustrates an alignment of MUT (SEQ ID NO:3) with the subject codon-optimized synMUT sequence (SEQ ID NO:1).

FIG. 5 illustrates an alignment of the codon-optimized synMUT polynucleotide sequence (SEQ ID NO:1) with the polypeptide sequence of MUT (SEQ ID NO:2) and further illustrates the exonic variants seen in MUT that are present in synMUT. The numeral 1 displayed indicate changes seen in MUT in an exome analysis that are found in synMUT. The numeral 2 displayed in the figure indicates unique synMUT variants at a position where MUT variants exist.

FIG. 11 shows an incidence of hepatocellular carcinoma following AAV Delivery-Mut+/− mice were either untreated (n=51), treated with 1-2×10$^{11}$ GC of AAV8-CBA-MUT (n=13) or 1-2×10$^{11}$ GC of AAV8-hAAT-synMUT (n=5) by intrahepatic injection at birth. *=P<0.01, NS=not statistically significant from untreated control group.

DETAILED DESCRIPTION

Figure 6:
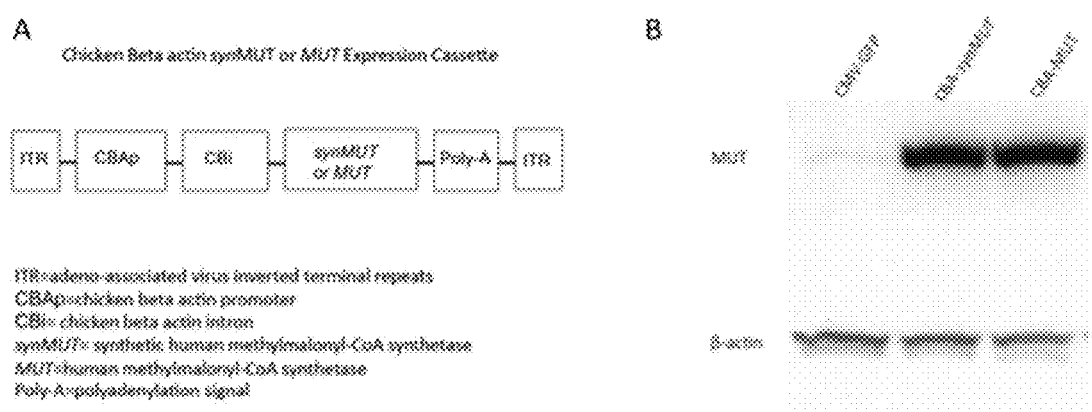
FIG. 6 illustrates the expression of MUT protein following transfection of HEK-293 cells in vitro with green fluorescent protein (GFP), optimized human methylmalonyl-CoA mutase polynucleotide (synMUT) (SEQ ID NO:1), or naturally-occurring human methylmalonyl-CoA mutase gene (MUT) (SEQ ID NO:3).

Reference will now be made in detail to representative embodiments of the invention. While the invention will be described in conjunction with the enumerated embodiments, it will be understood that the invention is not intended to be limited to those embodiments. On the contrary, the invention is intended to cover all alternatives, modifications, and equivalents that may be included within the scope of the present invention as defined by the claims.

One skilled in the art will recognize many methods and materials similar or equivalent to those described herein, which could be used in and are within the scope of the practice of the present invention. The present invention is in no way limited to the methods and materials described.

All publications, published patent documents, and patent applications cited in this application are indicative of the level of skill in the art(s) to which the application pertains. All publications, published patent documents, and patent applications cited herein are hereby incorporated by reference to the same extent as though each individual publication, published patent document, or patent application was specifically and individually indicated as being incorporated by reference.

Definitions

Unless defined otherwise, technical and scientific terms used herein have the same meaning as commonly understood by one of ordinary skill in the art to which this invention belongs. Although any methods, devices, and materials similar or equivalent to those described herein can be used in the practice or testing of the invention, the preferred methods, devices, and materials are now described.

As used in this application, including the appended claims, the singular forms "a," "an," and "the" include plural references, unless the content clearly dictates otherwise, and are used interchangeably with "at least one" and "one or more." Thus, reference to "a polynucleotide" includes a plurality of polynucleotides or genes, and the like.

As used herein, the term "about" represents an insignificant modification or variation of the numerical value such that the basic function of the item to which the numerical value relates is unchanged.

As used herein, the terms "comprises," "comprising," "includes," "including," "contains," "containing," and any variations thereof, are intended to cover a non-exclusive inclusion, such that a process, method, product-by-process, or composition of matter that comprises, includes, or contains an element or list of elements does not include only those elements but may include other elements not expressly listed or inherent to such process, method, product-by-process, or composition of matter.

In the context of synMUT, the terms "gene" and "transgene" are used interchangeably. A "transgene" is a gene that has been transferred from one organism to another.

The term "subject", as used herein, refers to a domesticated animal, a farm animal, a primate, a mammal, for example, a human.

The phrase "substantially identical", as used herein, refers to an amino acid sequence exhibiting high identity with a reference amino acid sequence (for example, at least 80%, at least 85%, at least 90%, at least 95%, at least 98%, or at least 99% identity) and retaining the biological activity of interest (the enzyme activity).

The polynucleotide sequences encoding synMUT allow for increased expression of the synMUT gene relative to naturally occurring human MUT sequences. These polynucleotide sequences are designed to not alter the naturally occurring human MUT amino acid sequence. They are also engineered or optimized to have increased transcriptional, translational, and protein refolding efficacy. This engineering is accomplished by using human codon biases, evaluating GC, CpG, and negative GpC content, optimizing the interaction between the codon and anti-codon, and eliminating cryptic splicing sites and RNA instability motifs. Because the sequences are novel, they facilitate detection using nucleic acid-based assays.

As used herein, "MUT" refers to human methylmalonyl coenzyme A mutase, and "Mut" refers to mouse methylmalonyl coenzyme A mutase. This protein catalyzes the isomerization of methylmalonyl-CoA to succinyl-CoA. This process requires 5'-deoxyadenosylcobalamin, a vitamin B12 derivative. Succinyl-CoA is a component of the citric acid cycle or tricarboxylic acid cycle (TCA). The gene encoding naturally occurring human methylmalonyl coenzyme A mutase gene is referred to as MUT. The polynucleotide encoding synthetic MUT is known as synMUT.

Naturally occurring human MUT is referred to as MUT, while synthetic MUT is designated as synMUT, even though the two are identical at the amino acid level.

"Codon optimization" refers to the process of altering a naturally occurring polynucleotide sequence to enhance expression in the target organism, e.g., humans. In the subject application, the human MUT gene has been altered to replace codons that occur less frequently in human genes with those that occur more frequently and/or with codons that are frequently found in highly expressed human genes.

As used herein, "determining", "determination", "detecting", or the like are used interchangeably herein and refer to the detecting or quantitation (measurement) of a molecule using any suitable method, including immunohistochemistry, fluorescence, chemiluminescence, radioactive labeling, surface plasmon resonance, surface acoustic waves, mass spectrometry, infrared spectroscopy, Raman spectroscopy, atomic force microscopy, scanning tunneling microscopy, electrochemical detection methods, nuclear magnetic resonance, quantum dots, and the like. "Detecting" and its variations refer to the identification or observation of the presence of a molecule in a biological sample, and/or to the measurement of the molecule's value.

As used herein, a "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In certain embodiments, it may be preferable to include isotonic agents, for example, sugars, polyalcohols such as mannitol, sorbitol, or sodium chloride in the composition.

A "therapeutically effective amount" refers to an amount effective, at dosages and for periods of time necessary, to achieve the desired therapeutic result. A therapeutically effective amount of a vector comprising the synthetic polynucleotide of the invention may vary according to factors such as the disease state, age, sex, and weight of the individual, and the ability of the vector to elicit a desired response in the individual. A therapeutically effective amount is also one in which any toxic or detrimental effects of the vector are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time, or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of the synthetic polynucleotide or a fragment thereof according to the invention calculated to produce the desired therapeutic effect in association with a pharmaceutical carrier.

Additional Embodiments of the Invention

The Synthetic Polynucleotide

In one embodiment of the invention, codon optimization was employed to create a highly active and synthetic MUT allele. This method involves determining the relative frequency of a codon in the protein-encoding genes in the human genome. For example, isoleucine can be encoded by AUU, AUC, or AUA, but in the human genome, AUC (47%), AUU (36%), and AUA (17%) are variably used to encode isoleucine in proteins. Therefore, in the proper sequence context, AUA would be changed to AUC to allow this codon to be more efficiently translated in human cells. FIG. 1 presents the codon usage statistics for a large fraction of human protein-encoding genes and serves as the basis for changing the codons throughout the MUT cDNA.

Thus, the invention comprises synthetic polynucleotides encoding methylmalonyl-CoA mutase (MUT) selected from the group consisting of the nucleic acid sequence of FIG. 2 (SEQ ID NO:1) and a polynucleotide sequence having at least about 80% identity thereto. For those polynucleotides having at least about 80% identity to SEQ ID NO:1, in additional embodiments, they have at least 85%, at least 90%, at least 95%, at least 97%, at least 98%, or at least 99% identity.

In one embodiment, the subject synthetic polynucleotide encodes a polypeptide with 100% identity to the naturally occurring human MUT protein, alternatively including naturally occurring alleles (FIG. 3). BLASTN alignment of MUT (NM_000255.3) with synMUT reveals 1721/2253 (76%) identities (FIG. 4); 532 bases are present in synMUT and not in MUT (NM_000255.3) (FIG. 4). To further validate that the synMUT sequence selected was sufficiently unique, 8600 exomes deposited in the NHLBI exome variant server (http://evs.gs.washington.edu/EVS/) were analyzed using NCBI's Align Specialized BLAST to compare the two sequences. 67 naturally occurring nucleotide changes in the MUT coding sequence resulted in synonymous alleles, missense variants, and missense mutations (Table 1). At nine of these 67 variant locations, synMUT possessed unique nucleotides that were not present in the exome database (FIG. 5). The synMUT therefore encodes 58 variants, present at variable frequencies (Table 1), identified in the exome database, and 474 unique base pairs, not present in the 8600 human exomes compared to MUT (NM_000255.3).

TABLE 1

Variants in syn-MUT not observed in the Exome data base

| Variant Position | Allelles Non-Coding Strand Bases | Allele Present on Coding Strand syn-MUT | All Allele # | MAF (%) | GVS Function | Amino Acid | Protein Pos. | cDNA Pos. |
|---|---|---|---|---|---|---|---|---|
| 6:49427127 | C/T | A | C = 1/T = 13005 | 0.0116/0.0/0.0077 | missense | ARG, GLN | 18/751 | 53 |
| 6:49427030 | G/C | G | G = 1/C = 13005 | 0.0/0.0227/0.0077 | missense | HIS, GLN | 50/751 | 150 |
| 6:49426975 | C/T | A | C = 39/T = 12967 | 0.3837/0.1362/0.2999 | missense | VAL, ILE | 69/751 | 205 |
| 6:49426939 | G/A | C | G = 1/A = 13005 | 0.0116/0.0/0.0077 | coding-synonymous | none | 81/751 | 241 |
| 6:49426895 | C/T | T | C = 3/T = 13003 | 0.0/0.0681/0.0231 | coding-synonymous | none | 95/751 | 285 |
| 6:49426896 | A/G | | A = 3/G = 13003 | 0.0/0.0681/0.0231 | missense | LEU, PRO | 95/751 | 284 |
| 6:49426853 | T/C | G | T = 1/C = 13005 | 0.0116/0.0/0.0077 | coding-synonymous | none | 109/751 | 327 |
| 6:49426814 | C/G | T | C = 1/G = 13005 | 0.0116/0.0/0.0077 | missense | LEU, PHE | 122/751 | 366 |
| 6:49425764 | T/C | G | T = 15/C = 12989 | 0.0/0.3404/0.1153 | coding-synonymous | none | 131/751 | 393 |
| 6:49425601 | C/T | A | C = 1/T = 13005 | 0.0116/0.0/0.0077 | missense | VAL, MET | 186/751 | 556 |
| 6:49425591 | C/T | A | C = 3/T = 13003 | 0.0/0.0681/0.0231 | missense | SER, ASN | 189/751 | 566 |
| 6:49425537 | A/C | G | A = 1/C = 13005 | 0.0/0.0227/0.0077 | missense | VAL, GLY | 207/751 | 620 |
| 6:49425521 | T/C | A | T = 7823/C = 5181 | 38.3578/42.7372/39.8416 | coding-synonymous | none | 212/751 | 636 |
| 6:49425446 | C/T | A | C = 138/T = 12854 | 1.3388/0.5225/1.0622 | coding-synonymous | none | 237/751 | 711 |
| 6:49425436 | C/T | A | C = 1/T = 12995 | 0.0/0.0227/0.0077 | missense | VAL, ILE | 241/751 | 721 |
| 6:49423948 | A/G | C | A = 1/G = 13003 | 0.0116/0.0/0.0077 | coding-synonymous | none | 252/751 | 756 |
| 6:49423923 | C/T | A | C = 1/T = 13005 | 0.0/0.0227/0.0077 | missense | VAL, ILE | 261/751 | 781 |
| 6:49423868 | C/T | A | C = 12/T = 12994 | 0.0/0.2724/0.0923 | missense | CYS, TYR | 279/751 | 836 |
| 6:49423826 | C/T | A | C = 13/T = 12993 | 0.1395/0.0227/0.1 | missense | ARG, GLN | 293/751 | 878 |
| 6:49421373 | T/C | G | T = 2/C = 13004 | 0.0/0.0454/0.0154 | missense | ILE, MET | 336/751 | 1008 |
| 6:49421345 | T/G | C | T = 1/G = 13005 | 0.0/0.0227/0.0077 | missense | ILE, LEU | 346/751 | 1036 |
| 6:49419403 | G/T | A | G = 1/T = 13005 | 0.0/0.0227/0.0077 | missense | PRO, THR | 370/751 | 1108 |
| 6:49419396 | G/A | T | G = 6/A = 13000 | 0.0698/0.0/0.0461 | missense | THR, ILE | 372/751 | 1115 |
| 6:49419386 | T/C | G | T = 22/C = 12984 | 0.2442/0.0227/0.1692 | missense | ILE, MET | 375/751 | 1125 |
| 6:49419305 | C/A | T | C = 1/A = 13005 | 0.0/0.0227/0.0077 | coding-synonymous | none | 402/751 | 1206 |

TABLE 1-continued

Variants in syn-MUT not observed in the Exome data base

| Variant Position | Allelles Non-Coding Strand Bases | Allele Present on Coding Strand | All syn-MUT | Allele # | MAF (%) | GVS Function | Amino Acid | Protein Pos. | cDNA Pos. |
|---|---|---|---|---|---|---|---|---|---|
| 6:49419241 | A/G | C | A = 1/G = 13005 | | 0.0/0.0227/0.0077 | missense | SER, PRO | 424/751 | 1272 |
| 6:49419214 | G/A | T | G = 1/A = 13005 | | 0.0116/0.0/0.0077 | missense | ARG, CYS | 433/751 | 1297 |
| 6.49419206 | A/T | A | A = 1/T = 13005 | | 0.0116/0.0/0.0077 | coding-synonymous | none | 435/751 | 1305 |
| 6:49416573 | T/C | G | T = 1/C = 13005 | | 0.0116/0.0/0.0077 | missense | GLN, ARG | 467/751 | 1400 |
| 6:49416571 | C/T | A | C = 1/T = 13005 | | 0.0116/0.0/0.0077 | missense | VAL, ILE | 468/751 | 1402 |
| 6:49416556 | A/C | G | A = 2/C = 13004 | | 0.0233/0.0/0.0154 | missense | SER, ALA | 473/751 | 1417 |
| 6:49416552 | T/C | G | T = 1/C = 13005 | | 0.0/0.0227/0.0077 | missense | GLN, ARG | 474/751 | 1421 |
| 6:49415450 | C/T | A | C = 1/T = 12997 | | 0.0116/0.0/0.0077 | missense | GLY, ASP | 498/751 | 1493 |
| 6:49415448 | T/C | G | T = 1343/C = 11655 | | 10.5655/9.8774/10.3324 | missense | THR, ALA | 499/751 | 1495 |
| 6:49415432 | C/G | C | C = 1/G = 12999 | | 0.0/0.0227/0.0077 | missense | GLY, ALA | 504/751 | 1511 |
| 6.49415384 | G/T | A | G = 1/T = 12997 | | 0.0116/0.0/0.0077 | missense-near-splice | THR, LYS | 520/751 | 1559 |
| 6:49412463 | C/T | A | C = 1/T = 13005 | | 0.0116/0.0/0.0077 | missense | ARG, LYS | 522/751 | 1566 |
| 6:49412458 | C/T | T | C = 1/T = 13005 | | 0.0/0.0227/0.0077 | missense | GLY, SER | 524/751 | 1570 |
| 6:49412433 | T/C | G | T = 4077/C = 8929 | | 36.6047/21.0849/31.3471 | missense | HIS, ARG | 532/751 | 1595 |
| 6.49412430 | T/C | G | T = 1/C = 13005 | | 0.0116/0.0/0.0077 | missense | TYR, CYS | 533/751 | 1598 |
| 6:49412421 | A/G | C | A = 1/G = 13005 | | 0.0/0.0227/0.0077 | missense | VAL, ALA | 536/751 | 1607 |
| 6:49412399 | A/G | C | A = 56/G = 12950 | | 0.6047/0.0908/0.4306 | coding-synonymous | none | 543/751 | 1629 |
| 6:49412398 | T/C | G | T = 1/C = 13005 | | 0.0/0.0227/0.0077 | missense | ARG, GLY | 544/751 | 1630 |
| 6:49409627 | T/C | C | T = 1/C = 13005 | | 0.0/0.0227/0.0077 | coding-synonymous | none | 578/751 | 1734 |
| 6:49409598 | NC | G | A = 3/C = 13003 | | 0.0/0.0681/0.0231 | missense | LEU, ARG | 588/751 | 1763 |
| 6:49409599 | A/G | A | A = 16/G = 12990 | | 0.0/0.3631/0.123 | missense | CYS, ARG | 588/751 | 1762 |
| 6:49409584 | G/C | G | G = 2/C = 13004 | | 0.0/0.0454/0.0154 | missense | GLN, GLU | 593/751 | 1777 |
| 6.49409569 | C/T | A | C = 2/T = 13004 | | 0.0/0.0454/0.0154 | missense | ALA, THR | 598/751 | 1792 |
| 6:49408037 | T/C | A | T = 1/C = 13005 | | 0.0/0.0227/0.0077 | missense | HIS, ARG | 613/751 | 1839 |
| 6:49408008 | T/C | G | T = 1/C = 13005 | | 0.0/0.0227/0.0077 | missense | ARG, GLY | 623/751 | 1867 |
| 6:49407995 | C/T | A | C = 1/T = 13005 | | 0.0116/0.0/0.0077 | missense | ARG, HIS | 627/751 | 1880 |
| 6.49407986 | T/C | G | T = 1/C = 13005 | | 0.0116/0.0/0.0077 | missense | GLU, GLY | 630/751 | 1889 |
| 6:49403334 | G/A | A | G = 1/A = 13005 | | 0.0116/0.0/0.0077 | coding-synonymous | none | 653/751 | 1959 |
| 6:49403324 | A/C | G | A = 1/C = 13005 | | 0.0/0.0227/0.0077 | missense | LEU, VAL | 657/751 | 1969 |
| 6:49403301 | T/C | T | T = 21/C = 12985 | | 0.0465/0.3858/0.1615 | coding-synonymous | none | 664/751 | 1992 |
| 6:49403302 | AG | C | A = 6/G = 13000 | | 0.0698/0.0/0.0461 | missense | VAL, ALA | 664/751 | 1991 |
| 6:49403282 | C/T | G | C = 7894/T = 5112 | | 38.3256/41.2165/39.3049 | missense | VAL, ILE | 671/751 | 2011 |
| 6:49403268 | G/A | A | G = 1/A = 13005 | | 0.0116/0.0/0.0077 | coding-synonymous | none | 675/751 | 2025 |
| 6:49403270 | T/C | G | T = 1/C = 13005 | | 0.0/0.0227/0.0077 | missense | THR, ALA | 675/751 | 2023 |
| 6.49403267 | T/C | G | T = 1/C = 13005 | | 0.0/0.0227/0.0077 | missense | THR, ALA | 676/751 | 2026 |
| 6:49403260 | C/T | A | C = 1/T = 13005 | | 0.0/0.0227/0.0077 | missense | ARG, HIS | 678/751 | 2033 |
| 6:49403194 | T/A | T | T = 1/A = 13005 | | 0.0116/0.0/0.0077 | missense | LYS, MET | 700/751 | 2099 |
| 6:49399544 | A/C | G | A = 3/C = 13003 | | 0.0/0.0681/0.0231 | missense | VAL, GLY | 717/751 | 2150 |
| 6.49399498 | A/G | A | A = 1/G = 13005 | | 0.0116/0.0/0.0077 | coding-synonymous | none | 732/751 | 2196 |
| 6:49399476 | T/C | G | T = 1/C = 13005 | | 0.0116/0.0/0.0077 | missense | LYS, GLU | 740/751 | 2218 |

In another aspect, SEQ ID NO:3 encodes MUT protein that has 100% identity with the naturally occurring human MUT protein, or that has at least 90% amino acid identity to the naturally occurring human MUT protein. In a preferred embodiment, the polynucleotide encodes MUT protein that has at least 95% amino acid identity to naturally occurring human MUT protein.

In one embodiment, a polypeptide according to the invention retains at least 90% of the naturally occurring human MUT protein function, i.e., the capacity to catalyze the conversion of L-methylmalonyl-CoA to succinyl-CoA. In another embodiment, the encoded MUT protein retains at least 95% of the naturally occurring human MUT protein function. This protein function can be measured, for example, via the efficacy to rescue a neonatal lethal phenotype in Mut knock-out mice (Chandler, et al. 2010 Mol Ther 18:11-6) (FIG. 9), the lowering of circulating metabolites including methylmalonic acid in a disease model of MMA (Chandler, et al. 2010 Mol Ther 18:11-6; Carrillo-Carrasco, et al. 2010 Hu Gene Ther 21:1147-54; Senac, et al. 2012 Gene Ther 19:385-91) (FIG. 10), the measurement of whole body (Chandler, et al. 2010 Mol Ther 18:11-6; Senac, et al. 2012 Gene Ther 19:385-91) or hepatic$^{1}$-C-$^{13}$propionate oxidative capacity (Carrillo-Carrasco, et al. 2010 Hu Gene Ther 21:1147-54), or the correction of macromolecular $^{1}$-C-$^{14}$propionate incorporation in cell culture (Chandler, et al. 2007 BMC Med Genet 8:64).

In some embodiments, the synthetic polynucleotide exhibits improved expression relative to the expression of naturally occurring human methylmalonyl-CoA mutase polynucleotide sequence. The improved expression is due to the polynucleotide comprising codons that have been optimized relative to the naturally occurring human methylmalonyl-CoA mutase polynucleotide sequence. In one aspect, the synthetic polynucleotide has at least about 25%, at least about 30%, at least about 35%, at least about 40%, at least about 45%, at least about 50%, at least about 55%, at least about 60%, at least about 65%, at least about 70%, at least about 75%, at least about 80% of less commonly used codons replaced with more commonly used codons. In additional embodiments, the polynucleotide has at least 85%, 90%, or 95% replacement of less commonly used codons with more commonly used codons, and demonstrate equivalent or enhanced expression of MUT as compared to SEQ ID NO:3

In some embodiments, the synthetic polynucleotide sequences of the invention preferably encode a polypeptide that retains at least about 80% of the enhanced MUT expression (as demonstrated by expression of the polynucleotide of SEQ ID NO:1 in an appropriate host.) In additional embodiments, the polypeptide retains at least 85%, 90%, or 95% or 100% of the enhanced expression observed with the polynucleotide of SEQ ID NO:1.

In designing the synMUT of the present invention, the following considerations were balanced. For example, the fewer changes that are made to the nucleotide sequence of SEQ ID NO:3, decreases the potential of altering the secondary structure of the sequence, which can have a significant impact on gene expression. The introduction of undesirable restriction sites is also reduced, facilitating the subcloning of MUT into the plasmid expression vector. However, a greater number of changes to the nucleotide sequence of SEQ ID NO:3 allows for more convenient identification of the translated and expressed message, e.g. mRNA, in vivo. Additionally, greater number of changes to the nucleotide sequence of SEQ ID NO:3 provides for increased likelihood of greater expression. These considerations were balanced when arriving at SEQ ID NO:1. The polynucleotide sequences encoding synMUT allow for increased expression of the synMUT gene relative to naturally occurring human MUT sequences. They are also engineered to have increased transcriptional, translational, and protein refolding efficacy. This engineering is accomplished by using human codon biases, evaluating GC, CpG, and negative GpC content, optimizing the interaction between the codon and anti-codon, and eliminating cryptic splicing sites and RNA instability motifs. Because the sequences are novel, they facilitate detection using nucleic acid-based assays.

MUT has a total of 750 amino acids and synMUT contains approximately 750 codons corresponding to said amino acids. Of these codons, in SEQ ID NO:1, approximately 463 codons are changed from that of the natural human MUT, however, as described, SEQ ID NO:1, despite changes from SEQ ID NO:3, codes for the amino acid sequence SEQ ID NO:2 for MUT. Codons for SEQ ID NO:1 are changed, in accordance with the equivalent amino acid positions of SEQ ID NO:2, at positions 2, 4, 5, 6, 8, 9, 10, 11, 12, 13, 14, 15, 17, 18, 19, 22, 23, 24, 25, 26, 27, 29, 30, 31, 32, 33, 36, 38, 39, 40, 41, 42, 44, 45, 47, 48, 49, 52, 59, 60, 63, 64, 65, 67, 68, 69, 70, 72, 73, 74, 75, 76, 77, 80, 81, 82, 83, 85, 90, 92, 93, 95, 96, 97, 98, 100, 103, 106, 107, 108, 110, 111, 112, 113, 117, 119, 120, 122, 128, 129, 130, 134, 135, 136, 137, 138, 141, 134, 147, 149, 150, 151, 152, 153, 154, 155, 156, 157, 160, 162, 164, 166, 170, 171, 173, 174, 177, 179, 180, 183, 184, 185, 187, 189, 190, 191, 192, 194, 195, 196, 198, 199, 200, 201, 203, 204, 206, 207, 208, 210, 211, 212, 213, 214, 215, 216, 217, 218, 219, 220, 221, 222, 224, 225, 227, 228, 230, 234, 235, 241, 243, 244, 245, 246, 247, 248, 249, 250, 254, 255, 256, 257, 220, 262, 263, 264, 270, 271, 272, 273, 278, 279, 280, 281, 284, 285, 286, 287, 289, 290, 292, 294, 298, 299, 300, 301, 302, 303, 304, 305, 306, 308, 312, 314, 315, 316, 318, 319, 320, 323, 325, 326, 328, 330, 332, 333, 335, 337, 342, 343, 344, 345, 346, 347, 348, 349, 350, 351, 352, 355, 357, 358, 360, 362, 363, 364, 365, 369, 370, 372, 373, 377, 378, 379, 381, 382, 384, 385, 388, 389, 392, 393, 394, 395, 396, 397, 398, 400, 401, 403, 405, 406, 407, 409, 411, 412, 413, 414, 416, 417, 418, 419, 420, 422, 424, 427, 432, 433, 434, 436, 437, 438, 432, 434, 435, 439, 450, 453, 456, 457, 458, 459, 462, 463, 464, 466, 467, 468, 469, 472, 473, 474, 475, 476, 477, 478, 479, 480, 481, 482, 483, 485, 486, 487, 488, 489, 494, 495, 499, 500, 502, 504, 505, 507, 508, 509, 511, 512, 513, 516, 517, 518, 520, 523, 524, 525, 527, 528, 529, 530, 532, 533, 534, 535, 536, 537, 538, 539, 542, 544, 545, 547, 548, 551, 553, 555, 556, 558, 560, 561, 563, 566, 567, 570, 571, 572, 573, 574, 575, 576, 577, 578, 581, 584, 585, 586, 588, 590, 591, 592, 594, 597, 598, 599, 600 604, 605, 606, 609, 610, 612, 613, 614, 615, 616, 617, 618, 619, 621, 624, 625, 626, 628, 629, 633, 635, 636, 637, 638, 640, 641, 642, 644, 646, 627, 630, 633, 634, 635, 636, 637, 638, 661, 662, 663, 664, 667, 668, 669, 670, 671, 672, 673, 674, 675, 677, 679, 681, 682, 683, 686, 689, 691, 692, 693, 694, 696, 697, 698, 701, 702, 703, 705, 707, 710, 711, 714, 715, 716, 717, 718, 719, 720, 721, 722, 723, 724, 725, 726, 727, 728, 729, 731, 732, 733, 734, 735, 736, 740, 743, 745, 746, 748, 749, 750 of SEQ ID NO:2, relative to the natural human sequence SEQ ID NO:3. In this embodiment, the amino acid sequence for natural human MUT has been retained.

It can be appreciated that partial reversion of the designed synMUT to codons that are found in MUT can be expected to result in nucleic acid sequences that, when incorporated into appropriate vectors, can also exhibit the desirable properties of SEQ ID NO:1, for example, such partial reversion variants can have equivalent expression of MUT from a vector inserted into an appropriate host, as SEQ ID NO: 1. For example, the invention includes nucleic acids in which at least about 1 altered codon, at least about 2 altered codons, at least about 3, altered codons, at least about 4 altered codons, at least about 5 altered codons, at least about 6 altered codons, at least about 7 altered codons, at least about 8 altered codons, at least about 9 altered codons, at least about 10 altered codons, at least about 11 altered codons, at least about 12 altered codons, at least about 13 altered codons, at least about 14 altered codons, at least about 15 altered codons, at least about 16 altered codons, at least about 17 altered codons, at least about 18 altered codons, at least about 20 altered codons, at least about 25 altered codons, at least about 30 altered codons, at least about 35 altered codons, at least about 40 altered codons, at least about 50 altered codons, at least about 55 altered codons, at least about 60 altered codons, at least about 65 altered codons, at least about 70 altered codons, at least about 75 altered codons, at least about 80 altered codons, at least about 85 altered codons, at least about 90 altered codons, at least about 95 altered codons, at least about 100 altered codons, at least about 110 altered codons, at least about 120 altered codons, at least about 130 altered codons, at least about 130 altered codons, at least about 140 altered codons, at least about 150 altered codons, at least about 160 altered codons, at least about 170 altered codons, at least about 180 altered codons, at least about 190 altered codons, at least about 200 altered codons, at least about 220 altered codons, at least about 240 altered codons, at least about 260 altered codons, at least about 280 altered codons, at least about 300 altered codons, at least about 320 altered codons, at least about 340 altered codons, at least about 360 altered codons, at least about 380 altered codons, at least about 400 altered codons, at least about 420 altered codons, at least about 440 altered codons, at least about 460 altered codons, or at least about 480 of the altered codon positions in SEQ ID NO:1 are reverted to native codons according to SEQ ID NO:3, an alternate codon sequence for an amino acid sequence as shown in FIG. 1, or to SEQ ID NO:3 containing SNPs (alleles) as noted in Table 1, and having equivalent expression to SEQ ID NO:1. Alternately, at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100% of the altered codon positions in SEQ ID NO:1 are reverted to native sequence according to SEQ ID NO:3, an alternate codon sequence for an amino acid sequence as shown in FIG. 1, or to SEQ ID NO:3 containing SNPs as noted in Table 1, and having equivalent expression to SEQ ID NO:1.

In some embodiments, polynucleotides of the present invention do not share 100% identity with SEQ ID NO:3. In other words, in some embodiments, polynucleotides having 100% identity with SEQ ID NO:3 are excluded from the embodiments of the present invention.

The synthetic polynucleotide can be composed of DNA and/or RNA or a modified nucleic acid, such as a peptide nucleic acid, and could be conjugated for improved biological properties.

Therapy

In another aspect, the invention comprises a method of treating a disease or condition mediated by methylmalonyl-CoA mutase. The disease or condition can, in one embodiment, be methylmalonic acidemia (MMA). This method comprises administering to a subject in need thereof a synthetic methylmalonyl-CoA mutase polynucleotide construct comprising the synthetic polynucleotides (synMUT) described herein. The MUT enzyme is processed after transcription, translation, and translocation into the mitochondrial inner space. During this importation and maturation process, amino acids 1-32 are removed to produce the mature MUT peptide, comprised of residues 33-750. Thus, in another embodiment, the invention includes the portion of the synMUT enzyme located inside the mitochondrial matrix, specifically, residues 33-750 corresponding to nucleotides 62-2250 of synMUT, attached to a carrier, synthetic or heterologous mitochondrial leader sequence, charged or lipophilic small molecule to direct toward the mitochondria; conjugated or covalently modified to a peptide that targets the mitochondrial matrix; or encapsulated to deliver this fragment of synMUT to a subcellular organelle, cell type or tissue.

Enzyme replacement therapy consists of administration of the functional enzyme (methylmalonyl-CoA mutase) to a subject in a manner so that the enzyme administered will catalyze the reactions in the body that the subject's own defective or deleted enzyme cannot. In enzyme therapy, the defective enzyme can be replaced in vivo or repaired in vitro using the synthetic polynucleotide according to the invention. The functional enzyme molecule can be isolated or produced in vitro, for example. Methods for producing recombinant enzymes in vitro are known in the art. In vitro enzyme expression systems include, without limitation, cell-based systems (bacterial (for example, *Escherichia coli*, *Corynebacterium, Pseudomonas fluorescens*), yeast (for example, *Saccharomyces cerevisiae, Pichia Pastoris*), insect cell (for example, Baculovirus-infected insect cells, non-lytic insect cell expression), and eukaryotic systems (for example, *Leishmania*)) and cell-free systems (using purified RNA polymerase, ribosomes, tRNA, ribonucleotides). Viral in vitro expression systems are likewise known in the art. The enzyme isolated or produced according to the above-iterated methods exhibits, in specific embodiments, 80%, 85%, 90%, 95%, 98%, 99%, or 100% homology to the naturally occurring (for example, human) methylmalonyl-CoA mutase.

Gene therapy can involve in vivo gene therapy (direct introduction of the genetic material into the cell or body) or ex vivo gene transfer, which usually involves genetically altering cells prior to administration. In one aspect, genome editing, or genome editing with engineered nucleases (GEEN) may be performed with the synMUT nucleotides of the present invention allowing synMUT DNA to be inserted, replaced, or removed from a genome using artificially engineered nucleases. Any known engineered nuclease may be used such as Zinc finger nucleases (ZFNs), Transcription Activator-Like Effector Nucleases (TALENs), the CRISPR/Cas system, and engineered meganuclease re-engineered homing endonucleases. Alternately, the nucleotides of the present invention including synMUT, in combination with a CASP/CRISPR, ZFN, or TALEN can be used to engineer correction at the locus in a patient's cell either in vivo or ex vivo, then, in one embodiment, use that corrected cell, such as a fibroblast or lymphoblast, to create an iPS or other stem cell for use in cellular therapy.

Administration/Delivery and Dosage Forms

Routes of delivery of a synthetic methylmalonyl-Co-A mutase (MUT) polynucleotide according to the invention may include, without limitation, injection (systemic or at target site), for example, intradermal, subcutaneous, intravenous, intraperitoneal, intraocular, subretinal, renal artery, hepatic vein, intramuscular injection; physical, including ultrasound(-mediated transfection), electric field-induced molecular vibration, electroporation, transfection using laser irradiation, photochemical transfection, gene gun (particle bombardment); parenteral and oral (including inhalation aerosols and the like). Related methods include using genetically modified cells, antisense therapy, and RNA interference.

Vehicles for delivery of a synthetic methylmalonyl-CoA mutase polynucleotide (synMUT) according to the invention may include, without limitation, viral vectors (for example, AAV, adenovirus, baculovirus, retrovirus, lentivirus, foamy virus, herpes virus, Moloney murine leukemia virus, Vaccinia virus, and hepatitis virus) and non-viral vectors (for example, naked DNA, mini-circles, liposomes, ligand-polylysine-DNA complexes, nanoparticles, cationic polymers, including polycationic polymers such as dendrimers, synthetic peptide complexes, artificial chromosomes, and polydispersed polymers). Thus, dosage forms contemplated include injectables, aerosolized particles, capsules, and other oral dosage forms.

In certain embodiments, the vector used for gene therapy comprises an expression cassette. The expression cassette may, for example, consist of a promoter, the synthetic polynucleotide, and a polyadenylation signal. Viral promoters include, for example, the ubiquitous cytomegalovirus immediate early (CMV-IE) promoter, the chicken beta-actin (CBA) promoter, the simian virus 40 (SV40) promoter, the Rous sarcoma virus long terminal repeat (RSV-LTR) promoter, the Moloney murine leukemia virus (MoMLV) LTR promoter, and other retroviral LTR promoters. The promoters may vary with the type of viral vector used and are well-known in the art.

In one specific embodiment, synMUT could be placed under the transcriptional control of a ubiquitous or tissue-specific promoter, with a 5' intron, polyadenylation signal, and mRNA stability element, such as the woodchuck post-transcriptional regulatory element. The use of a tissue-specific promoter can restrict unwanted transgene expression, as well as facilitate persistent transgene expression. The therapeutic transgene could then be delivered as coated or naked DNA into the systemic circulation, portal vein, or directly injected into a tissue or organ, such as the liver or kidney. In addition to the liver or kidney, the brain, pancreas, eye, heart, lungs, bone marrow, and muscle may constitute targets for therapy. Other tissues or organs may be additionally contemplated as targets for therapy.

In another embodiment, the same synMUT expression construct could be packaged into a viral vector, such as an adenoviral vector, retroviral vector, lentiviral vector, or adeno-associated viral vector, and delivered by various means into the systemic circulation, portal vein, or directly injected into a tissue or organ, such as the liver or kidney. In addition to the liver or kidney, the brain, pancreas, eye, heart, lungs, bone marrow, and muscle may constitute targets for therapy. Other tissues or organs may be additionally contemplated as targets for therapy.

Tissue-specific promoters include, without limitation, Apo A-I, ApoE, hAAT, transthyretin, liver-enriched activator, albumin, PEPCK, and $RNAP_{II}$ promoters (liver), PAI-1, ICAM-2 (endothelium), MCK, SMC α-actin, myosin heavy-chain, and myosin light-chain promoters (muscle), cytokeratin 18, CFTR (epithelium), GFAP, NSE, Synapsin I, Preproenkephalin, dβH, prolactin, and myelin basic protein promoters (neuronal), and ankyrin, α-spectrin, globin, HLA-DRα, CD4, glucose 6-phosphatase, and dectin-2 promoters (erythroid).

Regulable promoters (for example, ligand-inducible or stimulus-inducible promoters) are also contemplated for expression constructs according to the invention.

In yet another embodiment, synMUT could be used in ex vivo applications via packaging into a retro- or lentiviral vector to create an integrating vector that could be used to permanently correct any cell type from a patient with MUT deficiency. The synMUT-transduced and corrected cells could then be used as a cellular therapy. Examples might include CD34+ stem cells, primary hepatocytes, or fibroblasts derived from patients with MUT deficiency. Fibroblasts could be reprogrammed to other cell types using iPS methods well known to practitioners of the art. In yet another embodiment, synMUT could be recombined using genomic engineering techniques that are well known to practitioners of the art, such as ZFNs and TALENS, into the MUT locus, a genomic safe harbor site, such as AAVS1, or into another advantageous location, such as into rDNA, the albumin locus, GAPDH, or a suitable expressed pseudogene.

A composition (pharmaceutical composition) for treating an individual by gene therapy may comprise a therapeutically effective amount of a vector comprising the synMUT transgenes or a viral particle produced by or obtained from same. The pharmaceutical composition may be for human or animal usage. Typically, a physician will determine the actual dosage which will be most suitable for an individual subject, and it will vary with the age, weight, and response of the particular individual.

The composition may, in specific embodiments, comprise a pharmaceutically acceptable carrier, diluent, excipient, or adjuvant. Such materials should be non-toxic and should not interfere with the efficacy of the transgene. Pharmaceutically acceptable excipients include, but are not limited to, liquids such as water, saline, glycerol, sugars and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in Remington's Pharmaceutical Sciences [Mack Pub. Co., 18th Edition, Easton, Pa. (1990)]. The choice of pharmaceutical carrier, excipient, or diluent can be selected with regard to the intended route of administration and standard pharmaceutical practice. The pharmaceutical compositions may comprise as, or in addition to, the carrier, excipient, or diluent any suitable binder(s), lubricant(s), suspending agent(s), coating agent(s), solubilizing agent(s), and other carrier agents that may aid or increase the viral entry into the target site (such as for example a lipid delivery system). For oral administration, excipients such as starch or lactose may be used. Flavoring or coloring agents may be included, as well. For parenteral administration, a sterile aqueous solution may be used, optionally containing other substances, such as salts or monosaccharides to make the solution isotonic with blood.

A composition according to the invention may be administered alone or in combination with at least one other agent, such as a stabilizing compound, which may be administered in any sterile, biocompatible pharmaceutical carrier, including, but not limited to, saline, buffered saline, dextrose, and water. The compositions may be administered to a patient alone, or in combination with other agents, modulators, or drugs (e.g., antibiotics).

The composition may be in a variety of forms. These include, for example, liquid, semi-solid and solid dosage forms, such as liquid solutions (e.g., injectable and infusible solutions), dispersions or suspensions, tablets, pills, powders, liposomes and suppositories. Additional dosage forms contemplated include: in the form of a suppository or pessary; in the form of a lotion, solution, cream, ointment or dusting powder; by use of a skin patch; in capsules or ovules; in the form of elixirs, solutions, or suspensions; in the form of tablets or lozenges.

EXAMPLES

Cell Culture Studies:

A synthetic codon-optimized human methylmalonyl-Co-A mutase gene (synMUT) was engineered using an iterative approach, wherein the naturally occurring MUT cDNA (NCBI Reference Sequence: NM_000255.31 was optimized codon by codon to create synMUT (FIG. 2) using OptimumGene™ codon optimization software (Genscript Inc) that incorporates critical factors involved in protein expression, such as codon adaptability, mRNA structure, and various cis-elements in transcription and translation. The resulting sequence that was selected had the maximal divergence from the MUT cDNA at the nucleotide level yet retained optimally utilized codons at each position.

To improve the expression of methylmalonyl-CoA mutase and create a vector that could express the human MUT gene in a more efficient fashion, synMUT was cloned using restriction endonuclease excision and DNA ligation into an expression vector under the control of the chicken β-actin promoter (Chandler, et al. 2010 *Mol Ther* 18:11-6). The construct expressing either the full-length MUT or the full-length synMUT was then transfected into 293FT cells using Lipofectamine™ (Life Technologies). Cloning and transfection methods are well understood by practitioners of the art (Sambrook, Fritsch, Maniatis. Molecular Cloning: A Laboratory Manual). After 48 hours, cellular protein was extracted from the transfected cells and evaluated for methylmalonyl-CoA mutase protein expression using Western analysis (Chandler, et al. 2010 *Mol Ther* 18:11-6). The results show that synMUT is transcribed and translated as or more efficiently than MUT (FIG. 6). FIG. 6 shows expression of MUT protein following transfection of HEK-293 cells in vitro with synMUT. FIG. 6(A) shows schematic of the expression constructs prepared as described in Chandler, et al. 2010 *Mol Ther* 18:11-6. Figure (B) shows HEK-293 cells transfected with green fluorescent protein (GFP), human codon optimized methylmalonyl-CoA mutase (labeled CBA-synMUT) or human methylmalonyl-CoA mutase (labeled CBA-MUT) expression construct. Cells transfected with CBA-synMUT exhibited a significant increase in the expression of MUT in comparison to cells transfected with GFP or CBA-MUT.

Gene Therapy in Methylmalonyl-CoA Mutase Knock-Out ($Mut^{-/-}$) Mice.

The targeted Mut allele harbors a deletion of exon 3 in the Mut gene. This exon encodes the putative substrate-binding pocket in the Mut enzyme. The Mut allele does not produce mature RNA, protein, or enzymatic activity. $Mut^{-/-}$ mice (mice having the Mut gene knocked out (disrupted or replaced) on a mixed (C57BL/6×[129SV/EvxFvBN]) background exhibit a semipenetrant neonatal lethal phenotype, with most mice perishing in the early neonatal period. In the instant example, the $Mut^{-/-}$ (methylmalonyl-CoA mutase knockout) mouse is also referred to as the mouse with MMA.

$Mut^{-/-}$ mice display massively elevated methylmalonic acid concentrations in the plasma that progressively rises to the 2 mmol/L range, until death occurs. $Mut^{+/-}$ animals have biochemical parameters identical to $Mut^{+/+}$ wild-type animals and were used as controls throughout. This animal model of MMA, therefore, recapitulates the severest form of the human condition—$mut^o$ methylmalonic acidemia.

The synMUT polynucleotide was then used to construct a series of novel gene therapy vectors to treat mice with MMA. One vector is designed to express synMUT in the liver of the MMA mouse and used to make a recombinant adeno-associated viral vector.

Figure 7:
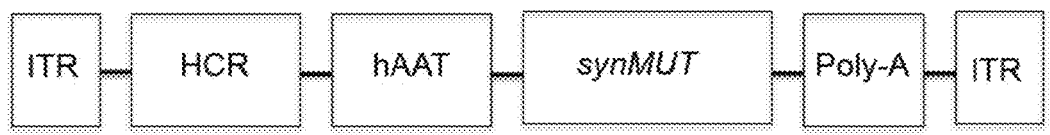
FIG. 7 presents a map of the AAV-HCR-hAAT-synMUT construct.

The AAV2/8-HCR-hAAT-RBG vector contains transcriptional control elements from the hepatic control region (HCR) and human alpha antitrypsin promoter (hAAT), cloning sites for the insertion of a complementary DNA, and the rabbit β-globin polyadenylation (RBG) signal (FIG. 7). Terminal repeats from AAV serotype 2 flank the expression cassette. The human codon-optimized methylmalonyl-CoA mutase (synMUT) was cloned into AAV2-HCR-hAAT-RBG and packaged into rAAV8 as previously described (Chandler, et al. 2010 Mol Ther 18:11-6), purified by cesium chloride centrifugation, and titered by qPCR to make the AAV8-HCR-hAAT-synMUT-RBG vector as previously described (Chandler, et al. 2010 Mol Ther 18:11-6; Carrillo-Carrasco, et al. 2010 Hum Gene Ther 21:1147-54). Animal studies were reviewed and approved by the National Human Genome Research Institute Animal User Committee. Hepatic injections were performed on non-anesthetized neonatal mice, typically within several hours after birth. Viral particles were diluted to a total volume of 20 microliters with phosphate-buffered saline immediately before injection and were delivered into the liver parenchyma using a 32-gauge needle and transdermal approach, as previously described.

Figure 8:
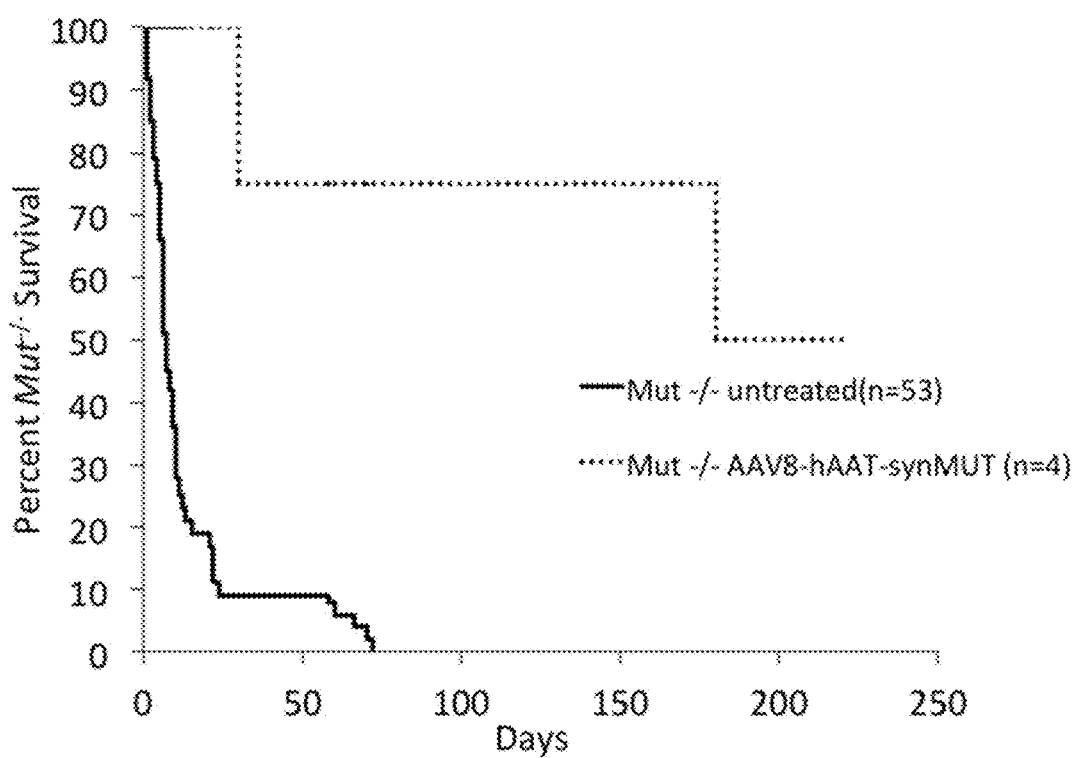
FIG. 8 illustrates the increased survival of Mut$^{-/-}$ mice after treatment with the AAV8-HCR-hAAT-synMUT construct.
Figure 9:
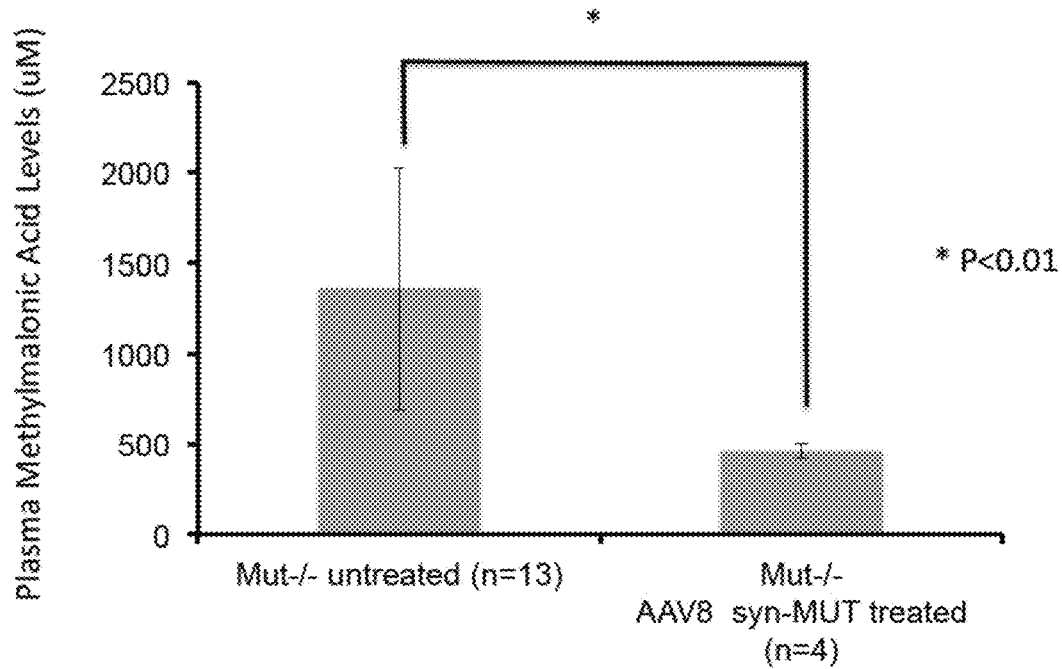
FIG. 9 illustrates the reduction in circulating metabolites in Mut mice after treatment with the AAV8-HCR-hAAT-synMUT construct.

Treatment with synMUT polynucleotide delivered using an AAV (adeno-associated virus) rescued the $Mut^{-/-}$ mice from neonatal lethality (FIG. 8), improved their growth, and lowered the levels of plasma methylmalonic acid in the blood (FIG. 9). This establishes the pre-clinical efficacy of synMUT as a treatment for MMA in vivo, including in other animal models, as well as in humans. FIG. 8 shows increased survival of Mut mice following treatment with AAV8-HCR-hAAT-synMUT. Mut mice received a single intra-hepatic injection of $1 \times 10^{11}$ GC of AAV8-HCR-hAAT-synMUT at birth. All of the treated Mut mice survived until day 30 and appeared normal relative to unaffected littermates. At day 30, a single treated Mut mouse was sacrificed to evaluate the in vivo expression of MUT (see FIG. 9). FIG. 9 shows metabolic correction after AAV8-HCR-hAAT-synMUT gene therapy. A significant reduction in the plasma MMA levels on day of life 90 were documented in Mut mice that received a single intra-hepatic injection of $1 \times 10^{11}$ GC of AAV8-HCR-hAAT-synMUT at birth.

Figure 10:
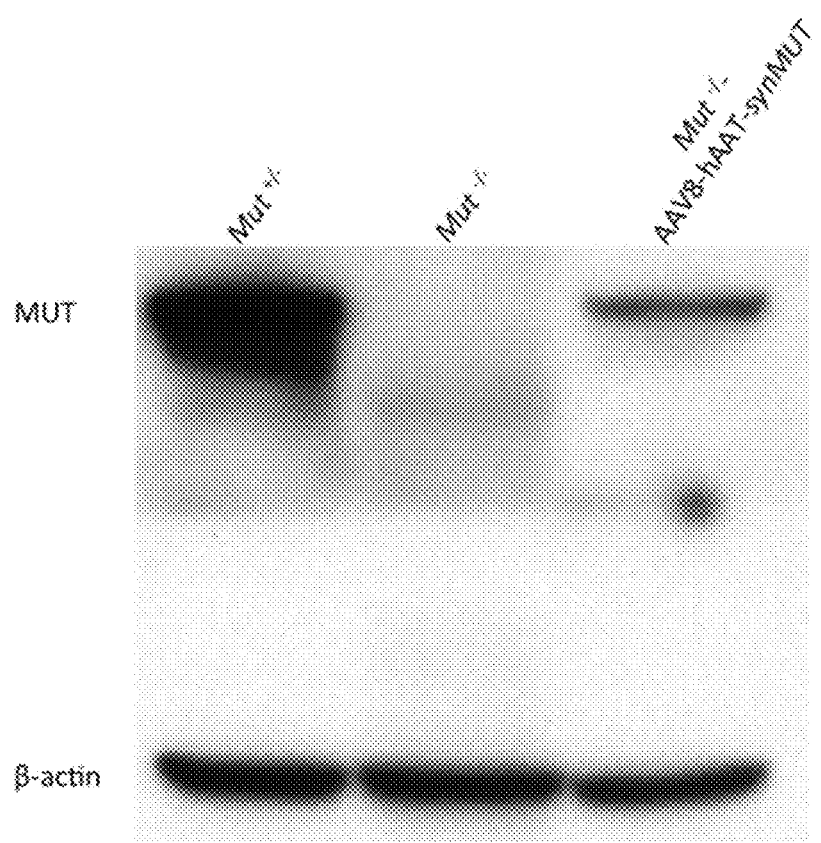
FIG. 10 shows expression of MUT in the liver after AAV8-HCR-hAAT-synMUT gene therapy.

A single treated $Mut^{-/-}$ mouse was sacrificed at 30 days after treatment with AAV2/8-HCR-hAAT-synMUT-RBG to evaluate in vivo expression of MUT (FIG. 10). FIG. 10 shows hepatic expression of MUT in a rescued Mut mouse following treatment with AAV8-HCR-hAAT-synMUT. The liver of the treated Mut mouse maintained a significant amount of MUT expression 30 days after treatment with AAV8-hAAT-synMUT, but less than that of untreated wild-type mice ($Mut^{+/-}$). By comparison, the liver of an untreated Mut mouse exhibited no detectable MUT protein.

It was observed that the liver of the treated $Mut^{-/-}$ mouse demonstrated continued expression of MUT at 30 days after treatment with AAV2/8-HCR-hAAT-synMUT-RBG, but less than that of untreated wild-type mice ($Mut^{+/+}$). The untreated $Mut^{-/-}$ mouse exhibited no detectable MUT protein expression.

Safety Study in Mice.

AAV genotoxicity, specifically hepatocarcinoma (HCC) in mice following AAV gene delivery, has been reported raising concerns about the safety of AAV gene therapy. We observed a similar increase in the occurrence of HCC following the treatment of mice with an AAV8-CBA-MUT we designed (FIG. 11). However, we do not observe any significant increase in the occurrence of HCC when mice are treated in a similar manner with AAV8-hAAT-synMUT. The data demonstrate that the AAV8-hAAT-synMUT is less genotoxic and has a better safety profile than that AAV8-CBA-MUT. These findings suggest that AAV8-hAAT-synMUT is a potentially safer AAV construct for human clinical trials.

The invention claimed is:

1. A method of treating a disease or condition mediated by methylmalonyl-CoA mutase, comprising administering to a subject in need thereof a therapeutic amount of a methylmalonyl-CoA mutase produced using a synthetic methylmalonyl-CoA mutase (MUT) polynucleotide (synMUT) selected from the group consisting of:
   (a) a polynucleotide comprising the nucleic acid sequence of SEQ ID NO:1; and
   (b) a codon-optimized polynucleotide comprising a polynucleotide having a nucleic acid sequence with at least about 80% identity to the nucleic acid sequence of SEQ ID NO:1 and encoding a polypeptide according to SEQ ID NO:2, and having equivalent expression in a host to either SEQ ID NO:1 expression or SEQ ID NO:3 expression,
   wherein the codon-optimized polynucleotide having at least about 80% identity to SEQ ID NO:1 does not have the nucleic acid sequence of SEQ ID NO:3.

2. The method of claim 1, wherein the disease or condition is methylmalonic academia (MMA).

3. The method of claim 1, wherein the polynucleotide has at least about 90% identity to the nucleic acid sequence of SEQ ID NO:1.

4. The method of claim 1, wherein the polynucleotide has at least about 95% identity to the nucleic acid sequence of SEQ ID NO:1.

5. The method of claim 1, wherein the polynucleotide has at least about 97% identity to the nucleic acid sequence of SEQ ID NO:1.

6. The method of claim 1, wherein the polynucleotide has at least about 99% identity to the nucleic acid sequence of SEQ ID NO:1.

7. The method of claim 1, wherein the synthetic methylmalonyl-CoA mutase (MUT) polynucleotide exhibits increased expression in an appropriate host relative to the expression SEQ ID NO:3 in an appropriate host.

8. The method of claim 7, wherein the synthetic polynucleotide having increased expression comprises a nucleic acid sequence comprising codons that have been optimized relative to the naturally occurring human methylmalonyl-CoA mutase polynucleotide sequence (SEQ ID NO:3).

9. The method of claim 7, wherein the nucleic acid sequence has at least about 70% of less commonly used codons replaced with more commonly used codons.

10. The method of claim 1, wherein the methylmalonyl-CoA mutase is formulated with a pharmaceutically acceptable carrier.

11. The method of claim 1, wherein the administering of the methylmalonyl-CoA mutase comprises administering an expression vector comprising the synthetic methylmalonyl-CoA mutase polynucleotide and expression of the polynucleotide in the subject.

* * * * *

SEQUENCE LISTING

```
<160> NUMBER OF SEQ ID NOS: 3

<210> SEQ ID NO 1
<211> LENGTH: 2253
<212> TYPE: DNA
<213> ORGANISM: Artificial Sequence
<220> FEATURE:
<223> OTHER INFORMATION: synMUT

<400> SEQUENCE: 1
atgctgagag ccaaaaacca gctgttcctg ctgagccccc actatctgag acaggtcaaa      60
```

```
gaaagttccg ggagtagact gatccagcag agactgctgc accagcagca gccactgcat    120
cctgagtggg ccgctctggc caagaaacag ctgaagggca aaaacccaga agacctgatc    180
tggcacactc cagaggggat ttcaatcaag cccctgtaca gcaaaaggga cactatggat    240
ctgccagagg aactgccagg agtgaagcct tcacccgcg accttaccc aactatgtat     300 acctttcgac cctggacaat tcggcagtac gccggcttca gtactgtgga ggaatcaaac    360
aagttttata aggacaacat caaggctgga cagcagggcc tgagtgtggc attcgatctg    420
gccacacatc gcggctatga ctcagataat cccagagtca gggggacgt gggaatggca     480 ggagtcgcta tcgacacagt ggaagatact aagattctgt tcgatggaat ccctctggag    540
aaaatgtctg tgagtatgac aatgaacggc gctgtcattc ccgtgctggc aaacttcatc    600
gtcactggcg aggaacaggg ggtgcctaag gaaaaactga ccggcacaat tcagaacgac    660
atcctgaagg agttcatggt gcggaatact tacattttc cccctgaacc atccatgaaa    720
atcattgccg atatcttcga gtacaccgct aagcacatgc caagttcaa ctcaattagc    780 atctccgggt atcatatgca ggaagcagga gccgacgcta ttctggagct ggcttacacc    840
ctggcagatg gcctggaata ttctcgaacc ggactgcagg caggcctgac aatcgacgag    900
ttcgctccta gactgagttt cttttgggga attggcatga acttttacat ggagatcgcc    960
aagatgaggc ctggccggag actgtgggca cacctgatcg agaagatgtt ccagcctaag   1020
aactctaaga gtctgctgct gcgggcccat tgccagacat ccggctggtc tctgactgaa   1080
caggacccat ataacaatat tgtcagaacc gcaatgaggc caatggcagc cgtgttcgga   1140
ggaacccaga gcctgcacac aaactccttt gatgaggccc tggggctgcc taccgtgaag   1200
tctgctagga ttgcacgcaa tacacagatc attatccagg aggaatccgg aatcccaaag   1260
gtggccgatc cctggggagg ctcttacatg atggagtgcc tgacaaacga cgtgtatgat   1320
gctgcactga agctgattaa tgaaatcgag gaaatggggg gaatggcaaa ggccgtggct   1380
gagggcattc caaaactgag gatcgaggaa tgtgcagcta ggcgccaggc acgaattgac   1440
tcaggaagcg aagtgatcgt cggggtgaat aagtaccagc tggagaaaga agacgcagtc   1500
gaagtgctgg ccatcgataa cacaagcgtg cgcaatcgac agattgagaa gctgaagaaa   1560
atcaaaagct cccgcgatca ggcactggcc gaacgatgcc tggcagccct gactgagtgt   1620
gctgcaagcg gggacggaaa cattctggct ctggcagtcg atgcctcccg gctagatgc    1680 actgtggggg aaatcaccga cgccctgaag aaagtcttcg gagagcacaa ggccaatgat   1740
cggatggtga gcggcgctta tagacaggag ttcggggaat ctaaagagat taccagtgcc   1800
atcaagaggg tgcacaagtt catggagaga aagggcgac ggcccaggct gctggtggca    1860
aagatgggac aggacggaca tgatcgcgga gcaaaagtca ttgccaccgg gttcgctgac   1920
ctgggatttg acgtggatat cggccctctg ttccagacac cacgagaggt cgcacagcag   1980
gcagtcgacg ctgatgtgca cgcagtcgga gtgtccactc tggcagctgg ccataagacc   2040
ctggtgcctg aactgatcaa agagctgaac tctctgggca gaccagacat cctggtcatg   2100
tgcggcggcg tgatcccacc ccaggattac gaattcctgt ttgaggtcgg ggtgagcaac   2160
gtgttcggac aggaaccag gatccctaag gccgcagtgc aggtcctgga tgatattgaa   2220
aagtgtctgg aaaagaaaca gcagtcagtg taa                                2253
```

<210> SEQ ID NO 2
<211> LENGTH: 750
<212> TYPE: PRT

<213> ORGANISM: Homo sapiens

<400> SEQUENCE: 2

```
Met Leu Arg Ala Lys Asn Gln Leu Phe Leu Ser Pro His Tyr Leu
1               5                   10                  15

Arg Gln Val Lys Glu Ser Ser Gly Ser Arg Leu Ile Gln Gln Arg Leu
            20                  25                  30

Leu His Gln Gln Gln Pro Leu His Pro Glu Trp Ala Ala Leu Ala Lys
        35                  40                  45

Lys Gln Leu Lys Gly Lys Asn Pro Glu Asp Leu Ile Trp His Thr Pro
    50                  55                  60

Glu Gly Ile Ser Ile Lys Pro Leu Tyr Ser Lys Arg Asp Thr Met Asp
65                  70                  75                  80

Leu Pro Glu Glu Leu Pro Gly Val Lys Pro Phe Thr Arg Gly Pro Tyr
                85                  90                  95

Pro Thr Met Tyr Thr Phe Arg Pro Trp Thr Ile Arg Gln Tyr Ala Gly
            100                 105                 110

Phe Ser Thr Val Glu Glu Ser Asn Lys Phe Tyr Lys Asp Asn Ile Lys
        115                 120                 125

Ala Gly Gln Gln Gly Leu Ser Val Ala Phe Asp Leu Ala Thr His Arg
    130                 135                 140

Gly Tyr Asp Ser Asp Asn Pro Arg Val Arg Gly Asp Val Gly Met Ala
145                 150                 155                 160

Gly Val Ala Ile Asp Thr Val Glu Asp Thr Lys Ile Leu Phe Asp Gly
                165                 170                 175

Ile Pro Leu Glu Lys Met Ser Val Ser Met Thr Met Asn Gly Ala Val
            180                 185                 190

Ile Pro Val Leu Ala Asn Phe Ile Val Thr Gly Glu Glu Gln Gly Val
        195                 200                 205

Pro Lys Glu Lys Leu Thr Gly Thr Ile Gln Asn Asp Ile Leu Lys Glu
    210                 215                 220

Phe Met Val Arg Asn Thr Tyr Ile Phe Pro Pro Glu Pro Ser Met Lys
225                 230                 235                 240

Ile Ile Ala Asp Ile Phe Glu Tyr Thr Ala Lys His Met Pro Lys Phe
                245                 250                 255

Asn Ser Ile Ser Ile Ser Gly Tyr His Met Gln Glu Ala Gly Ala Asp
            260                 265                 270

Ala Ile Leu Glu Leu Ala Tyr Thr Leu Ala Asp Gly Leu Glu Tyr Ser
        275                 280                 285

Arg Thr Gly Leu Gln Ala Gly Leu Thr Ile Asp Glu Phe Ala Pro Arg
    290                 295                 300

Leu Ser Phe Phe Trp Gly Ile Gly Met Asn Phe Tyr Met Glu Ile Ala
305                 310                 315                 320

Lys Met Arg Ala Gly Arg Arg Leu Trp Ala His Leu Ile Glu Lys Met
                325                 330                 335

Phe Gln Pro Lys Asn Ser Lys Ser Leu Leu Arg Ala His Cys Gln
        340                 345                 350

Thr Ser Gly Trp Ser Leu Thr Glu Gln Asp Pro Tyr Asn Asn Ile Val
    355                 360                 365

Arg Thr Ala Ile Glu Ala Met Ala Ala Val Phe Gly Gly Thr Gln Ser
    370                 375                 380

Leu His Thr Asn Ser Phe Asp Glu Ala Leu Gly Leu Pro Thr Val Lys
385                 390                 395                 400
```

```
Ser Ala Arg Ile Ala Arg Asn Thr Gln Ile Ile Gln Glu Glu Ser
                405                 410                 415
Gly Ile Pro Lys Val Ala Asp Pro Trp Gly Gly Ser Tyr Met Met Glu
            420                 425                 430
Cys Leu Thr Asn Asp Val Tyr Asp Ala Ala Leu Lys Leu Ile Asn Glu
            435                 440                 445
Ile Glu Glu Met Gly Gly Met Ala Lys Ala Val Ala Glu Gly Ile Pro
450                 455                 460
Lys Leu Arg Ile Glu Glu Cys Ala Ala Arg Arg Gln Ala Arg Ile Asp
465                 470                 475                 480
Ser Gly Ser Glu Val Ile Val Gly Val Asn Lys Tyr Gln Leu Glu Lys
                485                 490                 495
Glu Asp Ala Val Glu Val Leu Ala Ile Asp Asn Thr Ser Val Arg Asn
            500                 505                 510
Arg Gln Ile Glu Lys Leu Lys Lys Ile Lys Ser Ser Arg Asp Gln Ala
        515                 520                 525
Leu Ala Glu His Cys Leu Ala Ala Leu Thr Glu Cys Ala Ala Ser Gly
    530                 535                 540
Asp Gly Asn Ile Leu Ala Leu Ala Val Asp Ala Ser Arg Ala Arg Cys
545                 550                 555                 560
Thr Val Gly Glu Ile Thr Asp Ala Leu Lys Lys Val Phe Gly Glu His
                565                 570                 575
Lys Ala Asn Asp Arg Met Val Ser Gly Ala Tyr Arg Gln Glu Phe Gly
            580                 585                 590
Glu Ser Lys Glu Ile Thr Ser Ala Ile Lys Arg Val His Lys Phe Met
        595                 600                 605
Glu Arg Glu Gly Arg Arg Pro Arg Leu Leu Val Ala Lys Met Gly Gln
    610                 615                 620
Asp Gly His Asp Arg Gly Ala Lys Val Ile Ala Thr Gly Phe Ala Asp
625                 630                 635                 640
Leu Gly Phe Asp Val Asp Ile Gly Pro Leu Phe Gln Thr Pro Arg Glu
                645                 650                 655
Val Ala Gln Gln Ala Val Asp Ala Asp Val His Ala Val Gly Val Ser
            660                 665                 670
Thr Leu Ala Ala Gly His Lys Thr Leu Val Pro Glu Leu Ile Lys Glu
        675                 680                 685
Leu Asn Ser Leu Gly Arg Pro Asp Ile Leu Val Met Cys Gly Gly Val
    690                 695                 700
Ile Pro Pro Gln Asp Tyr Glu Phe Leu Phe Glu Val Gly Val Ser Asn
705                 710                 715                 720
Val Phe Gly Pro Gly Thr Arg Ile Pro Lys Ala Ala Val Gln Val Leu
                725                 730                 735
Asp Asp Ile Glu Lys Cys Leu Glu Lys Lys Gln Gln Ser Val
            740                 745                 750

<210> SEQ ID NO 3
<211> LENGTH: 2253
<212> TYPE: DNA
<213> ORGANISM: Homo sapiens

<400> SEQUENCE: 3
atgttaagag ctaagaatca gcttttttta ctttcacctc attacctgag gcaggtaaaa      60
gaatcatcag ctccaggct catacagcaa cgacttctac accagcaaca gccccttcac     120
ccagaatggg ctgccctggc taaaaagcag ctgaaaggca aaacccaga agacctaata     180
```

```
tggcacaccc cggaagggat ctctataaaa cccttgtatt ccaagagaga tactatggac      240
ttacctgaag aacttccagg agtgaagcca ttcacacgtg gaccatatcc taccatgtat      300
acctttaggc cctggaccat ccgccagtat gctggtttta gtactgtgga agaaagcaat      360
aagttctata aggacaacat taaggctggt cagcagggat tatcagttgc ctttgatctg      420
gcgacacatc gtggctatga ttcagacaac cctcgagttc gtggtgatgt tggaatggct      480
ggagttgcta ttgacactgt ggaagatacc aaaattcttt ttgatggaat tcctttagaa      540
aaaatgtcag tttccatgac tatgaatgga gcagttattc cagttcttgc aaattttata      600
gtaactggag aagaacaagg tgtacctaaa gagaagctta ctggtaccat ccaaaatgat      660
atactaaagg aatttatggt tcgaaataca tacattttc ctccagaacc atccatgaaa      720
attattgctg acatatttga atatacagca agcacatgc caaaatttaa ttcaatttca      780
attagtggat accatatgca ggaagcaggg gctgatgcca ttctggagct ggcctatact      840
ttagcagatg gattggagta ctctagaact ggactccagg ctggcctgac aattgatgaa      900
tttgcaccaa ggttgtcttt cttctgggga attggaatga atttctatat ggaaatagca      960
aagatgagag ctggtagaag actctgggct cacttaatag agaaaatgtt tcagcctaaa     1020
aactcaaaat ctcttcttct aagagcacac tgtcagacat ctggatggtc acttactgag     1080
caggatccct acaataatat tgtccgtact gcaatagaag caatggcagc agtatttgga     1140
gggactcagt ctttgcacac aaattctttt gatgaagctt tgggtttgcc aactgtgaaa     1200
agtgctcgaa ttgccaggaa cacacaaatc atcattcaag aagaatctgg gattcccaaa     1260
gtggctgatc cttggggagg ttcttacatg atggaatgtc tcacaaatga tgtttatgat     1320
gctgctttaa agctcattaa tgaaattgaa gaaatgggtg aatggccaa agctgtagct     1380 gagggaatac ctaaacttcg aattgaagaa tgtgctgccc gaagacaagc tagaatagat     1440
tctggttctg aagtaattgt tggagtaaat aagtaccagt tggaaaaaga gacgctgta      1500 gaagttctgg caattgataa tacttcagtg cgaaacaggc agattgaaaa acttaagaag     1560
atcaaatcca gcagggatca agcttttggct gaacgttgtc ttgctgcact aaccgaatgt     1620
gctgctagcg gagatggaaa tatcctggct cttgcagtgg atgcatctcg ggcaagatgt     1680
acagtgggag aaatcacaga tgccctgaaa aaggtatttg gtgaacataa agcgaatgat     1740
cgaatggtga gtgagcata tcgccaggaa tttggagaaa gtaaagagat aacatctgct     1800
atcaagaggg ttcataaatt catggaacgt gaaggtcgca gacctcgtct tcttgtagca     1860
aaaatgggac aagatggcca tgacagagga gcaaagtta tgctacagg atttgctgat     1920 cttggttttg atgtggacat aggccctctt ttccagactc ctcgtgaagt ggcccagcag     1980
gctgtggatg cggatgtgca tgctgtgggc ataagcaccc tcgctgctgg tcataaaacc     2040
ctagttcctg aactcatcaa agaacttaac tcccttggac ggccagatat tcttgtcatg     2100
tgtggagggg tgataccacc tcaggattat gaatttctgt ttgaagttgg tgtttccaat     2160
gtatttggtc ctgggactcg aattccaaag gctgccgttc aggtgcttga tgatattgag     2220
aagtgtttgg aaaagaagca gcaatctgta taa                                 2253
```